(12) United States Patent
Meridew et al.

(10) Patent No.: US 11,406,398 B2
(45) Date of Patent: Aug. 9, 2022

(54) PATIENT-SPECIFIC FEMOROACETABULAR IMPINGEMENT INSTRUMENTS AND METHODS

(71) Applicant: Biomet Manufacturing, LLC, Warsaw, IN (US)

(72) Inventors: Jason D. Meridew, Warsaw, IN (US); Paige Scott, West Lafayette, IN (US); Kristoff Corten, Herselt (BE)

(73) Assignee: Biomet Manufacturing, LLC, Warsaw, IN (US)

( * ) Notice: Subject to any disclaimer, the term of this patent is extended or adjusted under 35 U.S.C. 154(b) by 491 days.

(21) Appl. No.: 16/584,134

(22) Filed: Sep. 26, 2019

(65) Prior Publication Data

US 2020/0015896 A1  Jan. 16, 2020

Related U.S. Application Data

(63) Continuation of application No. 15/179,218, filed on Jun. 10, 2016, now Pat. No. 10,456,205, which is a (Continued)

(51) Int. Cl.
*A61B 17/16* (2006.01)
*A61B 34/00* (2016.01)
(Continued)

(52) U.S. Cl.
CPC .......... *A61B 17/1668* (2013.01); *A61B 17/15* (2013.01); *A61B 17/1666* (2013.01); *A61B 17/175* (2013.01); *A61B 17/1746* (2013.01); *A61B 34/00* (2016.02); *A61B 34/10* (2016.02); *A61B 2017/568* (2013.01); (Continued)

(58) Field of Classification Search
CPC .............. A61B 2034/108; A61B 34/10; A61B 17/1742; A61B 17/1633; A61B 17/1659; A61B 2090/063
See application file for complete search history.

(56) References Cited

U.S. PATENT DOCUMENTS 1,480,285 A   1/1924  Moore
2,181,746 A   11/1939 Siebrandt
(Continued)

FOREIGN PATENT DOCUMENTS

CA   2447694 A1   12/2002
CA   2501041 A1   4/2004
(Continued)

OTHER PUBLICATIONS

"3D-Implantatplanung und StereolithographieImplantatbohrschablonen", Stomatologie 101.3, (2004), 55-59.
(Continued)

*Primary Examiner* — Andrew Yang
(74) *Attorney, Agent, or Firm* — Schwegman Lundberg & Woessner, P.A.

(57) ABSTRACT

A device for a patient-specific acetabular and/or femoral guide. The guides can be used in a selected resection of at least one of a femur and an acetabulum to increase a range of motion of the femur relative to the acetabulum. Generally, a natural acetabulum and femoral head are maintained.

20 Claims, 12 Drawing Sheets

Related U.S. Application Data continuation of application No. 13/627,626, filed on Sep. 26, 2012, now Pat. No. 9,386,993.

(60) Provisional application No. 61/540,857, filed on Sep. 29, 2011.

(51) Int. Cl.
  *A61B 17/17* (2006.01)
  *A61B 17/15* (2006.01)
  *A61B 34/10* (2016.01)
  *B33Y 80/00* (2015.01)
  *A61B 17/56* (2006.01)

(52) U.S. Cl.
  CPC ... *A61B 2034/102* (2016.02); *A61B 2034/105* (2016.02); *A61B 2034/108* (2016.02); *B33Y 80/00* (2014.12)

(56) References Cited

U.S. PATENT DOCUMENTS

| | | |
|---|---|---|
| 2,407,845 A | 9/1946 | Orisan |
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,019,105 A | 5/1991 | Wiley |
| 5,030,219 A | 7/1991 | Matsen, III et al. |
| 5,030,221 A | 7/1991 | Buechel et al. |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,176,711 A | 1/1993 | Grimes |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |

(56) References Cited

U.S. PATENT DOCUMENTS

| | | |
|---|---|---|
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliot et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,925,049 A | 7/1999 | Gustilo et al. |
| 5,925,077 A | 7/1999 | Williamson et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,059,789 A | 5/2000 | Dinger |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,132,469 A | 10/2000 | Schroeder |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,416,553 B1 | 7/2002 | White et al. |
| 6,424,332 B1 | 7/2002 | Powell |
| 6,427,698 B1 | 8/2002 | Yoon et al. |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert et al. |
| 6,682,567 B1 | 1/2004 | Schroeder |
| 6,696,073 B2 | 2/2004 | Boyce et al. |
| 6,697,664 B2 | 2/2004 | Kienzle III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladiono |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |

(56) References Cited

U.S. PATENT DOCUMENTS

| | | |
|---|---|---|
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,995 B2 | 9/2006 | Crofford |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,206 B2 | 2/2008 | Steffensmeier et al. |
| 7,335,207 B1 | 2/2008 | Smith |
| 7,335,231 B2 | 2/2008 | Mclean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian et al. |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-schäffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,476 B2 | 4/2010 | Nevelos et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,714,927 B2 | 5/2010 | Terashima |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenfeld et al. |

(56) References Cited

U.S. PATENT DOCUMENTS

| | | |
|---|---|---|
| 8,298,237 B2 | 10/2012 | Schoenfeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskala et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 9,005,297 B2 | 4/2015 | Katrana et al. |
| 9,386,993 B2 | 7/2016 | Meridew et al. |
| 2001/0005797 A1 | 6/2001 | Barlow et al. |
| 2001/0011190 A1 | 8/2001 | Park |
| 2001/0021876 A1 | 9/2001 | Terril-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0111690 A1 | 8/2002 | Hyde |
| 2002/0120342 A1 | 8/2002 | Gibbs |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Stuart, Jr. et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0212459 A1 | 11/2003 | Gibbs |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0225369 A1 | 11/2004 | Lakin et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1 | 1/2005 | Gibbs |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |

(56) References Cited

U.S. PATENT DOCUMENTS

| | | |
|---|---|---|
| 2005/0071015 A1 | 3/2005 | Sekel |
| 2005/0075641 A1 | 4/2005 | Singhatat et al. |
| 2005/0096535 A1 | 5/2005 | De la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0143746 A1 | 6/2005 | Steffensmeier et al. |
| 2005/0148843 A1 | 7/2005 | Roose |
| 2005/0149042 A1 | 7/2005 | Metzger |
| 2005/0165420 A1* | 7/2005 | Cha .................. A61B 17/1633 606/150 |
| 2005/0171545 A1 | 8/2005 | Walsh et al. |
| 2005/0177245 A1 | 8/2005 | Leatherbury et al. |
| 2005/0197661 A1* | 9/2005 | Carrison .......... A61B 17/32002 606/170 |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100632 A1* | 5/2006 | Fell .................. A61B 17/1675 606/81 |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106391 A1 | 5/2007 | Ronk |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Callazo |

(56) References Cited

U.S. PATENT DOCUMENTS

| | | |
|---|---|---|
| 2008/0015605 A1 | 1/2008 | Collazo |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0005191 A1 | 2/2008 | Kammerzell et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1* | 10/2009 | White .................. A61B 17/175 606/88 |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0105011 A1 | 4/2010 | Karkar et al. |

(56) References Cited

U.S. PATENT DOCUMENTS

| | | |
|---|---|---|
| 2010/0114101 A1 | 5/2010 | Crofford |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152742 A1 | 6/2010 | Nevelos et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0002691 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0001071 A1 | 1/2012 | Frigg |
| 2012/0004662 A1* | 1/2012 | Torrie ............... A61B 17/1742 606/87 |
| 2012/0010619 A1 | 1/2012 | Barsoum |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041564 A1 | 2/2012 | Landon |
| 2012/0046526 A1* | 2/2012 | Boettner ........... A61B 17/1746 600/210 |
| 2012/0065640 A1 | 3/2012 | Metzger et al. |
| 2012/0071893 A1* | 3/2012 | Smith ................ A61B 34/10 606/130 |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0123423 A1* | 5/2012 | Fryman .............. A61B 17/175 606/89 |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Seifert et al. |
| 2012/0265208 A1 | 10/2012 | Smith |
| 2012/0271131 A1 | 10/2012 | Kling |
| 2012/0271314 A1 | 10/2012 | Stemniski et al. |

(56) References Cited

U.S. PATENT DOCUMENTS

| | | |
|---|---|---|
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brlanza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0004631 A1 | 2/2013 | Ranawat et al. |
| 2013/0035766 A1 | 2/2013 | Meridew |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenfeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2016/0278793 A1 | 9/2016 | Meridew et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2168507 A2 | 3/2010 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2442441 A | 4/2008 |
| GB | 2447702 A | 9/2008 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |

(56) References Cited

FOREIGN PATENT DOCUMENTS

| | | |
|---|---|---|
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |
| WO | WO-2013170872 A1 | 11/2013 |
| WO | WO-2014019712 A1 | 2/2014 |

OTHER PUBLICATIONS

"Amazing Precision. Beautiful Results. The next evolution of MAKOplasty® is here", MAKO Surgical Corp., (Feb. 2009), 6 pgs.

"U.S. Appl. No. 13/627,626, Non Final Office Action dated Aug. 5, 2015", 9 pgs.

"U.S. Appl. No. 13/627,626, Notice of Allowance dated Mar. 10, 2016", 6 pgs.

"U.S. Appl. No. 13/627,626, Response filed Feb. 24, 2015 to Restriction Requirement dated Dec. 24, 2014", 18 pgs.

"U.S. Appl. No. 13/627,626, Response filed Nov. 3, 2015 to Non Final Office Action dated Aug. 5, 2015", 17 pgs.

"U.S. Appl. No. 13/627,626, Restriction Requirement dated Dec. 24, 2014", 10 pgs.

"U.S. Appl. No. 15/179,218, Final Office Action dated Apr. 9, 2019", 6 pgs.

"U.S. Appl. No. 15/179,218, Non Final Office Action dated Nov. 26, 2018", 7 pgs.

"U.S. Appl. No. 15/179,218, Notice of Allowance dated Jun. 24, 2019", 6 pgs.

"U.S. Appl. No. 15/179,218, Preliminary Amendment filed Jul. 27, 2016", 8 pgs.

"U.S. Appl. No. 15/179,218, Response filed Jun. 10, 2019 to Final Office Action dated Apr. 9, 2019", 12 pgs.

"U.S. Appl. No. 15/179,218, Response fled Feb. 26, 2019 to Non Final Office Action dated Nov. 26, 2018", 14 pgs.

"Ascent Total Knee System", Biomet, Inc., (Oct. 31, 1999), 16 pgs.

"Australian Application Serial No. 2013222609, First Examiner Report dated Feb. 16, 2015", 5 pgs.

"Comprehensive® Reverse Shoulder System", Biomet Orthopedics brochure, (2009), 8 pgs.

"Comprehensive® Reverse Shoulder System Surgical Technique", Biomet Orthopedics, (2009-2012), 48 pgs.

"Comprehensive® Reverse Shoulder System Technical Design Features", Biomet Orthopedics, (2009), 3 pgs.

"Comprehensive® Shoulder System Surgical Technique", Biomet Orthopedics brochure, (2007), 1-53.

"Comprehensive® Total Shoulder System", Biomet Orthopedics brochure, (2011), 4 pgs.

"Customized Patient Instruments, Patient specific instruments for patient specific needs", DePuy Orthopaedics, Inc., (2008), 14 pgs.

"Customized Patient Instruments, Primary Cruciate Retaining Surgical Technique for use with the Sigma® Knee System Utilizing Specialist® 2 Instrumentation", DePuy Orthopaedics, Inc., (2008), 1-23.

"Discovery® Elbow System", Biomet Orthopedics, Inc., (Nov. 30, 2007), 3 pgs.

"Discovery® Elbow System Surgical Technique", Biomet Orthopedics, Inc., (Dec. 31, 2008), 1-25.

"European Application Serial No. 07809326.7, Examination Notification Art. 94(3) dated Jan. 22, 2015", 6 pgs.

"European Application Serial No. 07809326.7, Extended European Search Report dated Nov. 15, 2011", 6 pgs.

"European Application Serial No. 09731923.0, Examination Notification Art. 94(3) dated Feb. 10, 2015", 7 pgs.

"European Application Serial No. 10705064.3, Examination Notification Art. 94(3) dated Feb. 4, 2015", 6 pgs.

"European Application Serial No. 12724475.4, Examination Notification Art. 94(3) dated Nov. 24, 2014", 7 pgs.

"Great Britain Application Serial No. 1116054.6, Search Report dated Dec. 21, 2011", 4 pgs.

"Hipsextant Instructions of Use", Surgical Planning Associates, Inc., (2011), 19 pgs.

"International Application Serial No. PCT/EP2010/061630, International Search Report dated Nov. 30, 2010", 3 pgs.

"International Application Serial No. PCT/US2007/013223, International Preliminary Report on Patentability dated Dec. 24, 2008", 5 pgs.

"International Application Serial No. PCT/US2007/013223, International Search Report dated Nov. 26, 2007", 3 pgs.

"International Application Serial No. PCT/US2007/013223, Written Opinion dated Nov. 26, 2007", 4 pgs.

(56) References Cited

OTHER PUBLICATIONS

"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/056670, Written Opinion dated Mar. 2, 2010", 10 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.

(56) References Cited

OTHER PUBLICATIONS

"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion dated Apr. 14, 2014", 11 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"Is Subchondroplasty® Right for Me?", [Online] retrieved from the internet: <http://www.subchondroplast}'. . . com/about subchondroplast}'./is subchondroplasty right for >, (Jul. 1, 2013), 1 pg.
"Japanese Application Serial No. 2014-511538, Office Action dated Apr. 7, 2015", (W/ English Translation), 5 pgs.
"Knee tensor combined with laser femoral head locator", Research Disclosure, No. 507, (Jul. 2006), 903.
"MAX-Ti™ Modular Protrusio Cage", Surgical Technique brochure. Biomet Orthopedics, Inc., (2003), 10 pgs.
"MAX-Ti™ Modular Protrusio Cage", Surgical Technique brochure. Biomet Orthopedics, Inc., (2006), 12 pgs.
"Method for constructing an allograft sleeve", Research Disclosure, No. 476, (Dec. 2003), 1294.
"OSS™ Orthopaedic Salvage System, Femoral/Tibial Augmentation", Biomet Orthopedics, Inc. (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"PAR 5™ Protrusio Acetabular Reconstruction System", Biomet Orthopedics, Inc., (2006), 12 pgs.
"Patient Matched PMI Implants, C.A.M.R.A. 3-D Imaging", Brochure, Biomet, Inc., Form Y-BMI-191/013191, (1991), 6 pgs.
"Regenerex® Tibial Cone Augment, Surgical Technique Addendum to the Vanguard® SSK Revision System", brochure. Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics Brochure, (May 15, 2009), 1-8.
"Subchondroplasty", [Online] retrieved from the internet: <http://www.subchondroplasty.com/>, (Jul. 1, 2013), 1 pg.
"The Oxford® Partial Knee Surgical Technique", Biomet, (Feb. 2010), 1-38.

"TruMatch™ Personalized knee replacement solutions", SIGMA® DePuy Orthopaedics, Inc, tri-fold brochure, (2009), 2 pgs.
"Vanguard® PFR Partial Knee Patellofemoral Replacement System", Surgical Technique, Biomet Orthopaedics,, (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer® UniSpacer® Knee System", Zimmer, Inc., (2005), 4 pgs.
Beaule, P E, et al., "The Young Adult With Hip Impingement: Deciding on The Optimal Intervention", J Bone Joint Surg Am, (2009), 210-221.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use Of Computerized Tomography In The Measurement Of Glenoid Version", Journal of Bone & Joint Surgery Am. (JBJS) 1992;74, (Aug. 1992), 1032-1037.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2,, (2003), 221-229.
Hutmacher, Dietmar W, "Scaffolds in tissue engineering bone and cartilage", Biomaterials, 21(24), (2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants— clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.

(56) References Cited

OTHER PUBLICATIONS

Murphy, S B, et al., "The Hip Sextant: Navigation of Acetabular Component Orientation Using a Mechanical Instrument", (2009), 1 pg.

Nicholls, Paul M. D, "Trauma Grand Rounds PMI (Patient-Matched Implants)", Biomet Orthopedics, Inc.,, (Feb. 29, 2000), 1 pg.

Overhoff, H M, et al., "Total Knee Arthroplasty: Coordinate System Definition and Planning based on 3-D Ultrasound Image Volumes", CARS 2001, Elsevier Science B.V., (2001), 283-288.

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Thoma, W, et al., "Endoprothetischen Versorgung des Kniegelenks auf der Basis eines 3D-computertomographischen Subtraktionversfahrens", Topic: Computer-aided orthopedic surgery. Orthopedist 2000 29: Sprinqer Verlag W/ Original German Document, (2000), 641-644.

U.S. Appl. No. 13/627,626 U.S. Pat. No. 9,386,993, filed Sep. 26, 2012, Patient-Specific Femoroacetabular Impingement Instruments and Methods.

U.S. Appl. No. 15/179,218, filed Jun. 10, 2016, Patient-Specific Femoroacetabular Impingement Instruments and Methods.

* cited by examiner

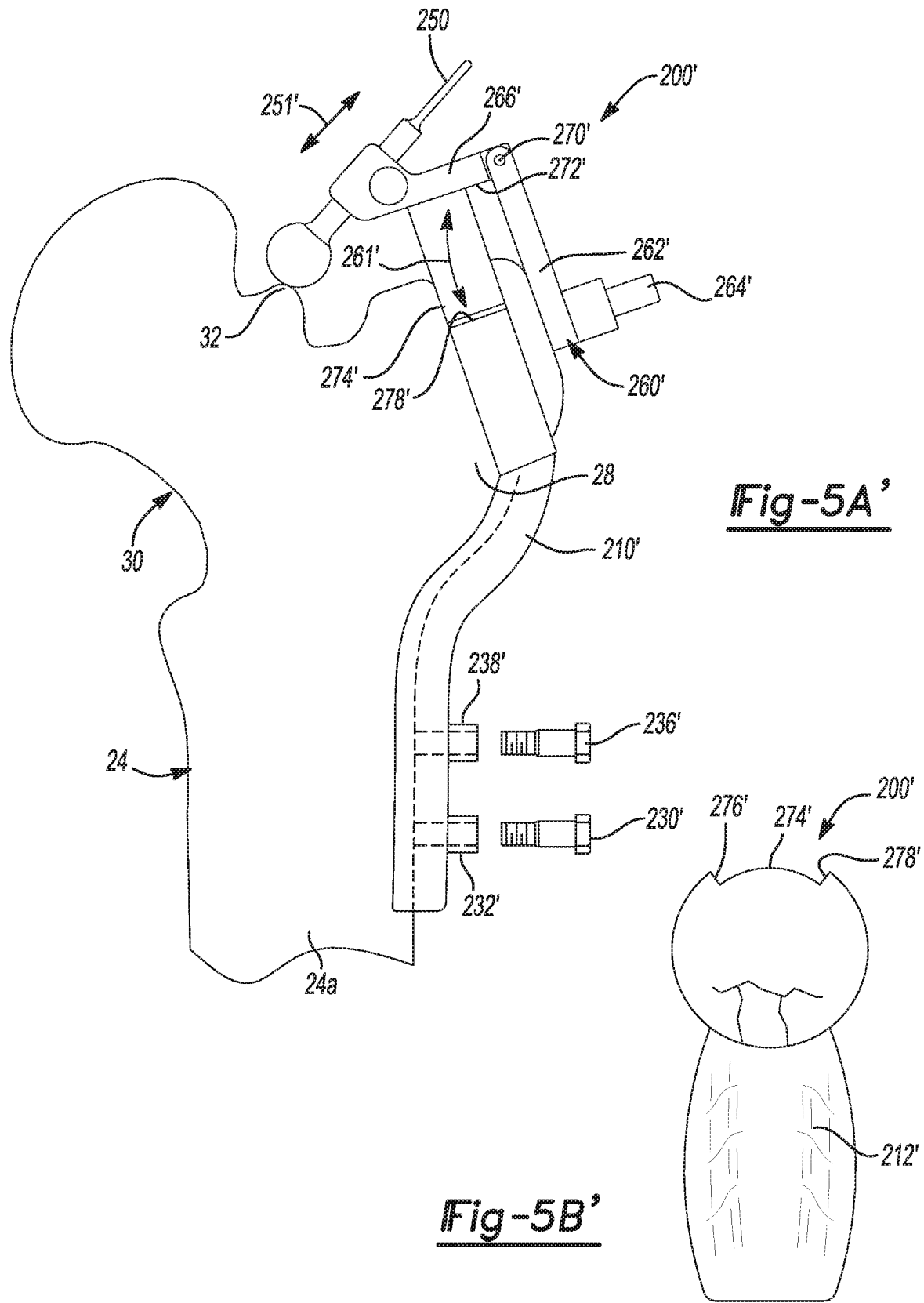

PATIENT-SPECIFIC FEMOROACETABULAR IMPINGEMENT INSTRUMENTS AND METHODS

CROSS-REFERENCE TO RELATED APPLICATIONS

This application claims the benefit of U.S. Provisional Application No. 61/540,857, filed on Sep. 29, 2011. The entire disclosure(s) of (each of) the above application(s) is (are) incorporated herein by reference.

INTRODUCTION

The present teachings provide patient-specific devices, which can include at least guides and implants, and methods for preparing one or both of a femur and an acetabulum for a selected range of motion, and particularly to increasing a range of motion of a natural femur within an acetabulum.

SUMMARY

This section provides a general summary of the disclosure, and is not a comprehensive disclosure of its full scope or all of its features.

A system is disclosed that can be used to design instruments for and perform a procedure on a specific patient. A patient-specific device can be a device that substantially matches a patient's anatomy, as discussed further herein, to perform a selected procedure on the patient. The patient-specific device is operable to conform to the anatomy of a single patient for performing the selected procedure. In other words, as discussed further herein, the patient specific device includes at least a surface that is designed to specifically engage the anatomy of a single patient in substantially a single position and orientation based on obtained information about a geometry of the single patient. This can include the contacting surface formed as a negative of a modeled positive geometry of the single patient The devices can include those that are operable to guide a mill or reamer instrument to remove a defect or abnormality from a selected portion of the anatomy. For example, a femur's articulation with an acetabulum (also referred to as femoroacetabular impingement). In femoroacetabular impingement, a femur, or a portion thereof, can have a bone abnormality that impinges on a portion of the acetabulum defined by the pelvis to limit a range of motion of the femur relative to the pelvis. Accordingly, a patient-specific device can be designed to assist in guiding or removal of a portion of at least one of the acetabulum or the femur of the patient to assist in increasing a range of motion of the femur relative to the pelvis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 6:
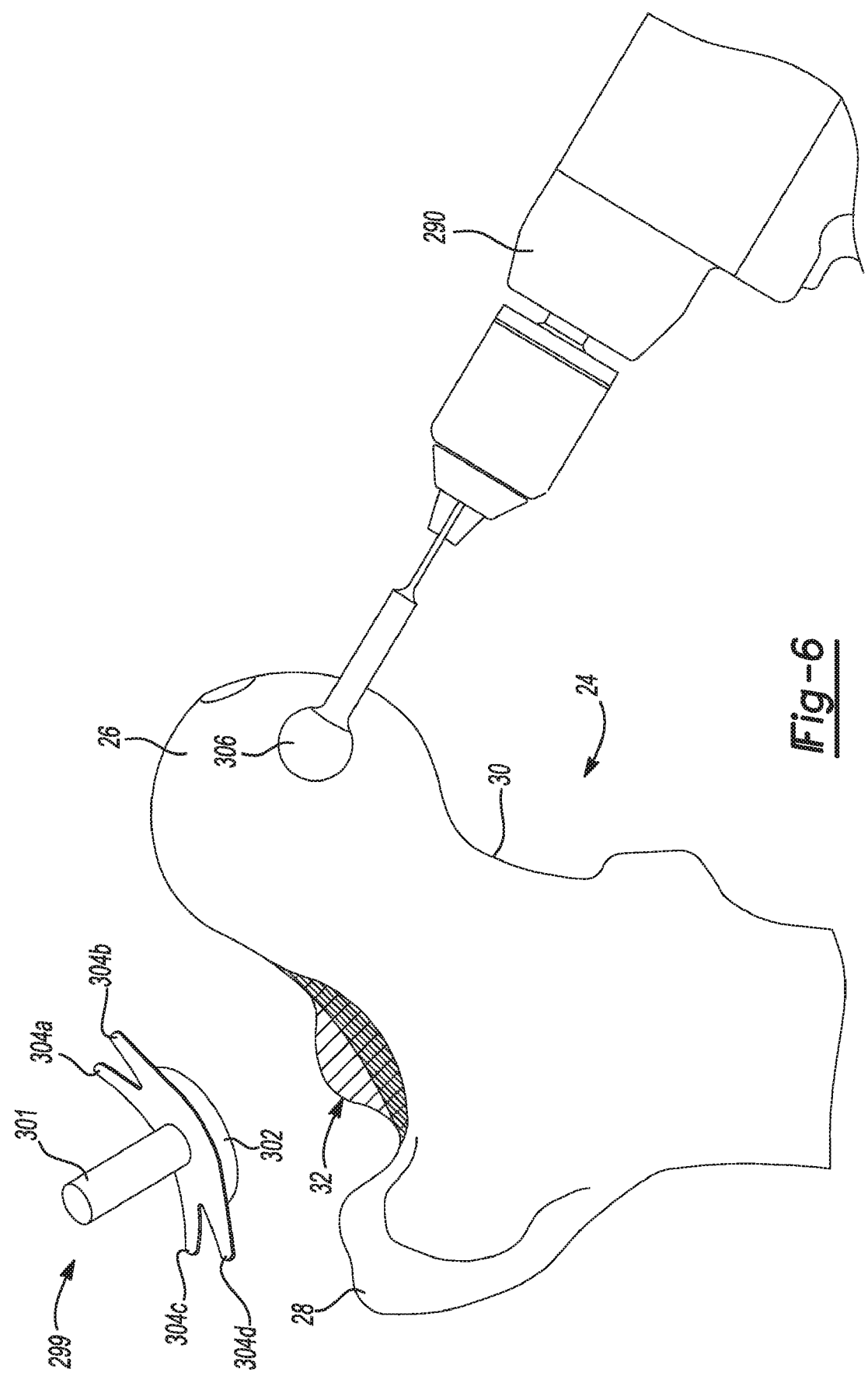
Figure 7:
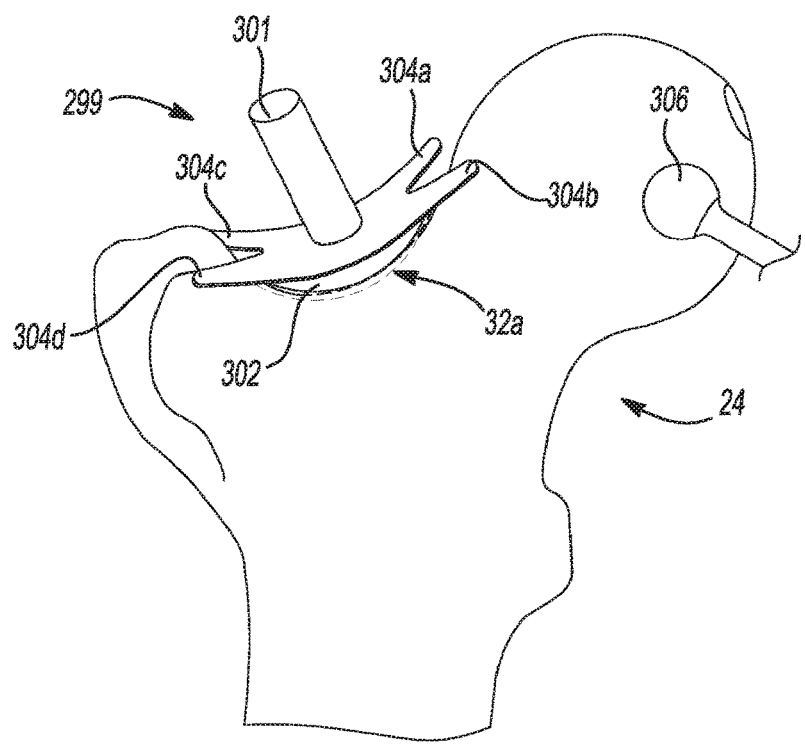
Figure 8:
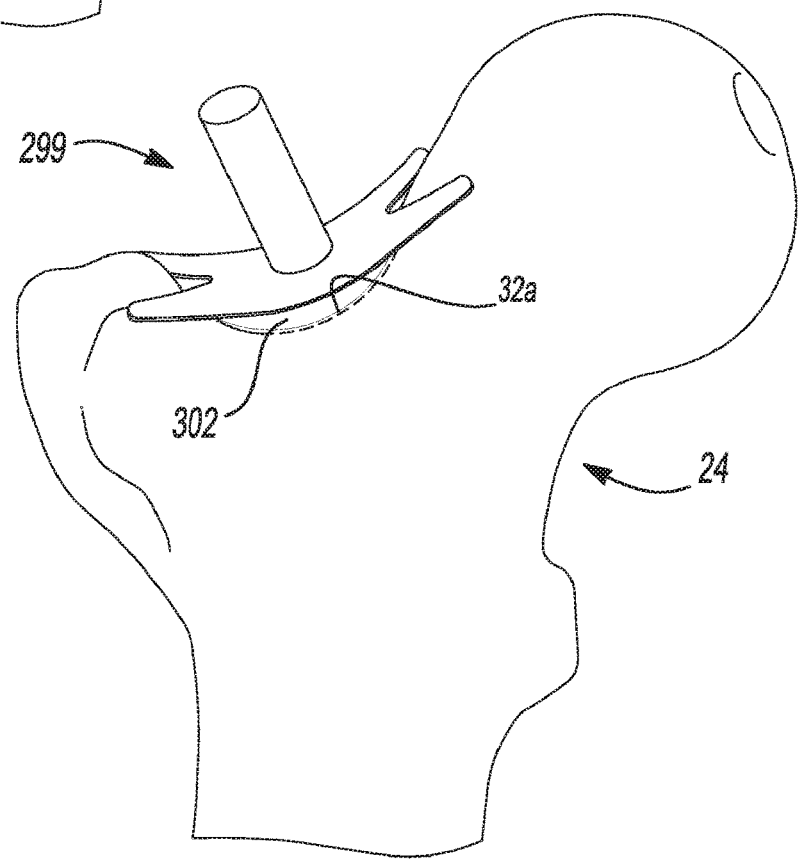
Figure 9:
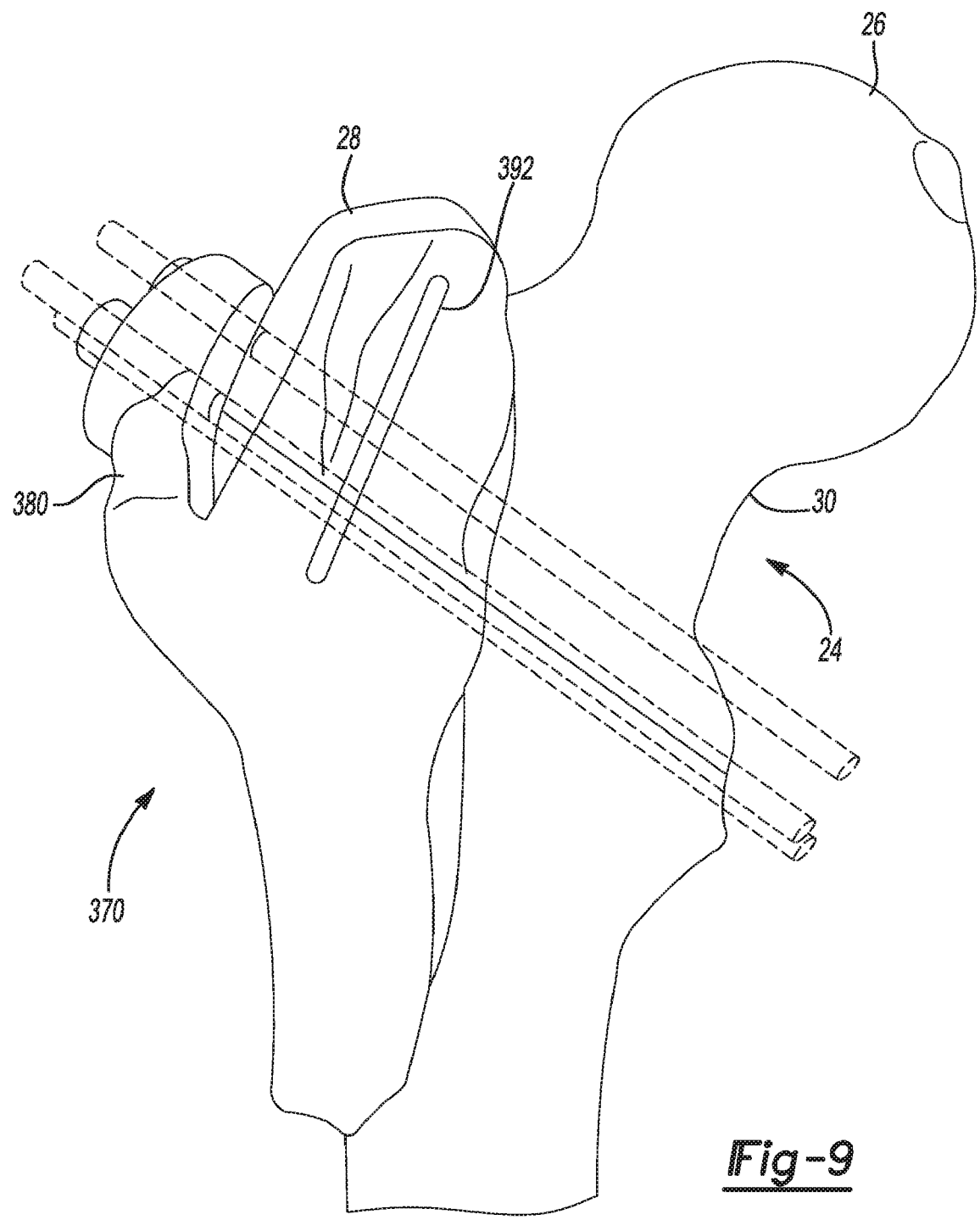
Figure 10:
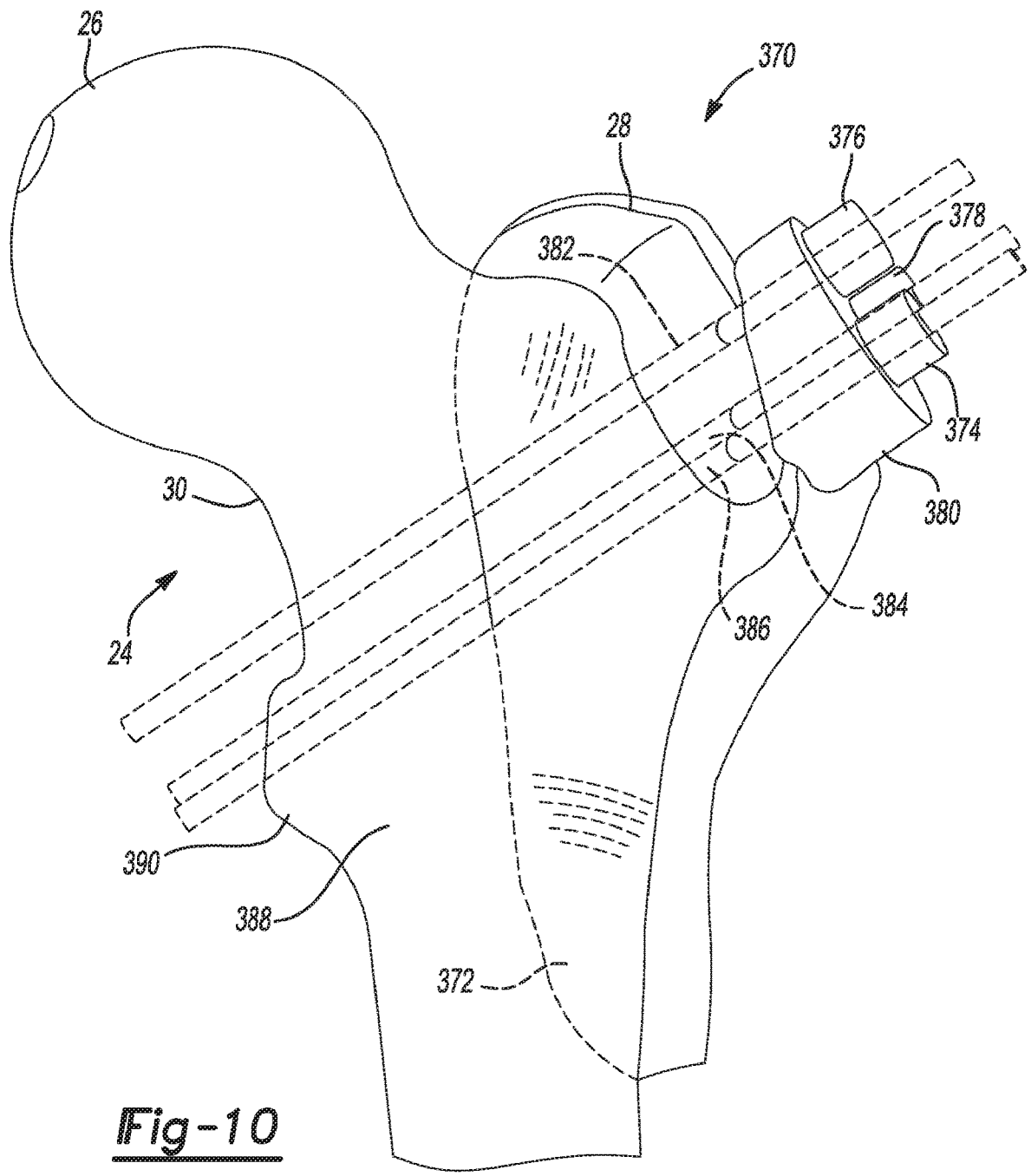
Figure 11:
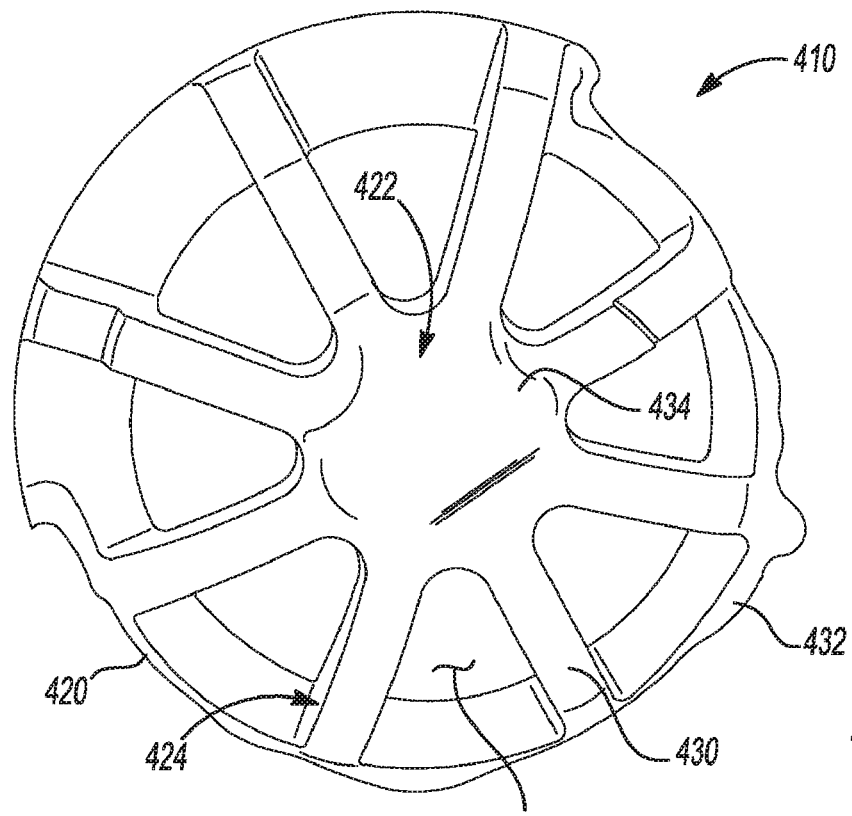
Figure 12:
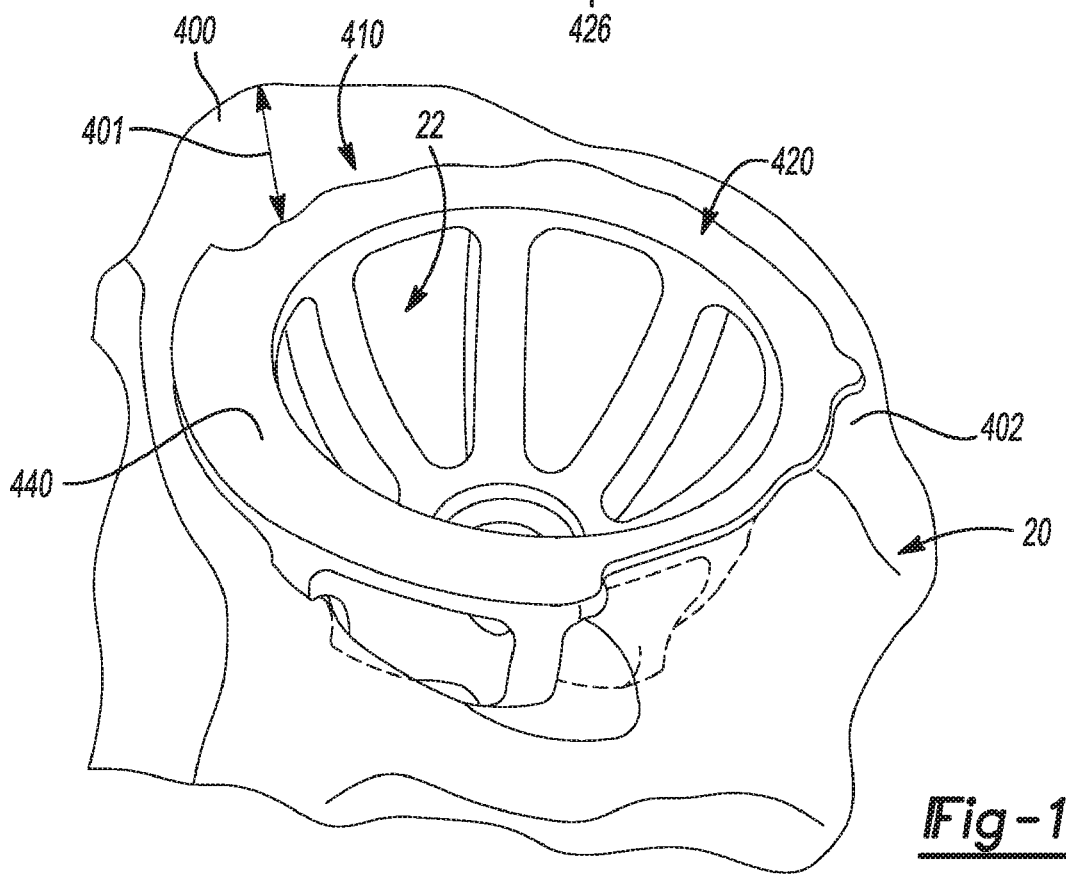

FIG. 5A' is an environmental view of a lateral femoral neck reamer guide;

FIG. 5B' is a bone contacting surface plan view of the lateral femoral neck reamer guide;

FIG. 6 is an environmental view of a template relative to a bone;

FIG. 7 is an environmental view of a template contacting a bone portion;

FIG. 8 is an environmental view of a second contact of the template to the bone portion after further resection as compared to FIG. 7;

FIG. 9 is a perspective view of a greater trochanter resection guide, according to various embodiments;

FIG. 10 is a second perspective view of the greater trochanter resection guide;

FIG. 11 is a bottom plan view of an acetabular resection guide, according to various embodiments;

FIG. 12 is a top environmental perspective view of the acetabular reamer; and

Figure 13:
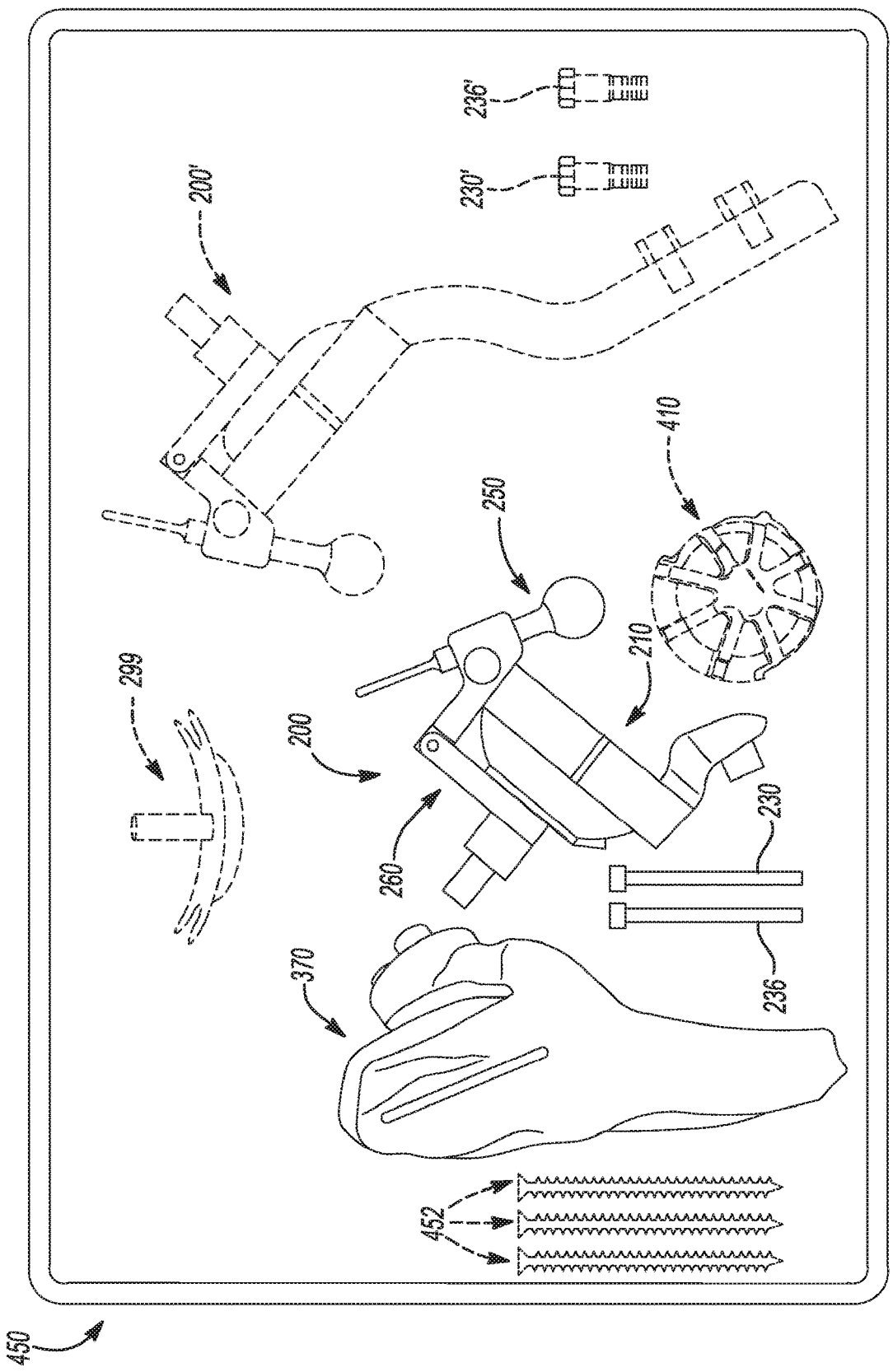

FIG. 13 is a top view of a kit of instruments and/or implants, according to various embodiments.

Corresponding reference numerals indicate corresponding parts throughout the several views of the drawings.

DETAILED DESCRIPTION

Exemplary embodiments will now be described more fully with reference to the accompanying drawings.

The present teachings generally provide a patient-specific (custom) guide and method for a selected arthroplasty of a patient, including partial acetabular socket resection, partial femoral resection and/or replacement or other similar procedure. More specifically, the present teachings provide a patient-specific guide for the acetabulum of the patient, when the acetabulum includes a defect that can be corrected by a partial socket resection or a partial implant. The present teachings also provide a patient-specific guide for the femur, including the femoral head and/or femoral neck of the patient, when the femoral head and/or neck includes a defect that can be corrected by a partial resection or a partial implant. Generally, patient-specific guides are those guides that are designed and manufactured based upon the specific anatomy geometry and configuration of a single selected patient. The specific geometry and configuration of the anatomy of the single patient is generally determined as discussed below (e.g. via modeling) and also generally based upon specific instructions from an intended user and/or implanter of the patient-specific devices.

Generally, patient-specific devices can be designed preoperatively using computer-assisted image methods based on three- or two-dimensional image data of the patient's anatomy reconstructed from magnetic resonance imaging (MRI), computed tomography (CT), ultrasound, X-ray, or other three- or two-dimensional medical scans of the patient's anatomy. In some cases patient-specific device design can be complemented with digital photography methods and/or anthropometry databases. Various CAD programs and/or software can be utilized for three-dimensional image reconstruction, such as, for example, software commercially available by Materialise USA, Plymouth, Mich.

Various alignment guides and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; U.S. patent application Ser. No. 12/025,414, filed Feb. 4, 2008, U.S. patent application Ser. No. 12/571,969, filed Oct. 1, 2009, and U.S. patent application Ser. No. 12/955,361, filed Nov. 29, 2010. The disclosures of the above applications are incorporated herein by reference.

In the preoperative planning stage for a femoroacetabular resection procedure, imaging data of the relevant anatomy of a single specific patient can be obtained at a medical facility or doctor's office, using one of medical imaging methods described above. The imaging data can include, for example, various medical scans of a relevant joint portion or other relevant portion of the single specific patient's anatomy, as needed for modeling, including three-dimensional (3D) modeling, further including 3D joint modeling. The image data can also be used, optionally, for implant alignment axis determination or for other alignment purposes. The imaging data thus obtained and other associated information can be used to construct a three-dimensional computer image of the joint or other portion of the anatomy of the single specific patient.

According to the present teachings, the patient-specific guides and implants are generally configured to match the anatomy of the single specific patient and are generally formed using computer modeling based on the single specific patient's reconstructed three-dimensional anatomic image. The patient-specific guides have an engagement surface that is made to conformingly contact and match a three-dimensional image/model of a bone surface of the single specific patient's (with or without cartilage or other soft tissue), by the computer methods discussed above. That is, a bone surface contacting surface of the patient-specific guide is intended to be a negative or similar to a mirror image of the bone surface of the single specific patient for which the patient-specific device is designed and manufactured. In this respect, a patient-specific guide can nestingly mate with the corresponding bone surface (with or without articular cartilage) of the single specific patient in only one position.

According to the present teachings, the patient-specific guide can include a custom-made (patient-specific) guiding formation, such as, for example, a mill guide for guiding a joint preparation tool, such as a reamer, cutter, broach, mill, drill or other cutting tool, according to the pre-operative plan for the patient. In some embodiments, the guiding formation can have a patient-specific size and shape configured during preoperative planning for the single specific patient to guide a milling tool, a reamer, a saw or other cutting tool, as discussed below. The preoperative plan can include planning for bone or joint preparation, including extent and area for defect removal, by milling, reaming, broaching or other cutting method, as well as implant selection and fitting. Also, a final or ideal range of motion can be selected.

The patient-specific guide described herein can be manufactured by various stereolithography methods, selective laser sintering, fused deposition modeling or other rapid prototyping methods. The patient-specific guide can be made of any biocompatible material, including metal, metal alloys or plastic. Generally, the patient-specific guide is made of lightweight materials, including polymers. The patient-specific implant can, however, also include or be formed entirely of any biocompatible materials, including metals and alloys. The patient-specific guide, implant and associated tools can be sterilized and shipped to the surgeon or medical facility in a kit for a specific patient and surgeon for use during the surgical procedure. The patient-specific guides may then be disposed after the procedure for which the patient-specific devices were designed and planned. Thus, the patient-specific devices as disclosed herein can be disposable or single procedure devices.

Figure 1:
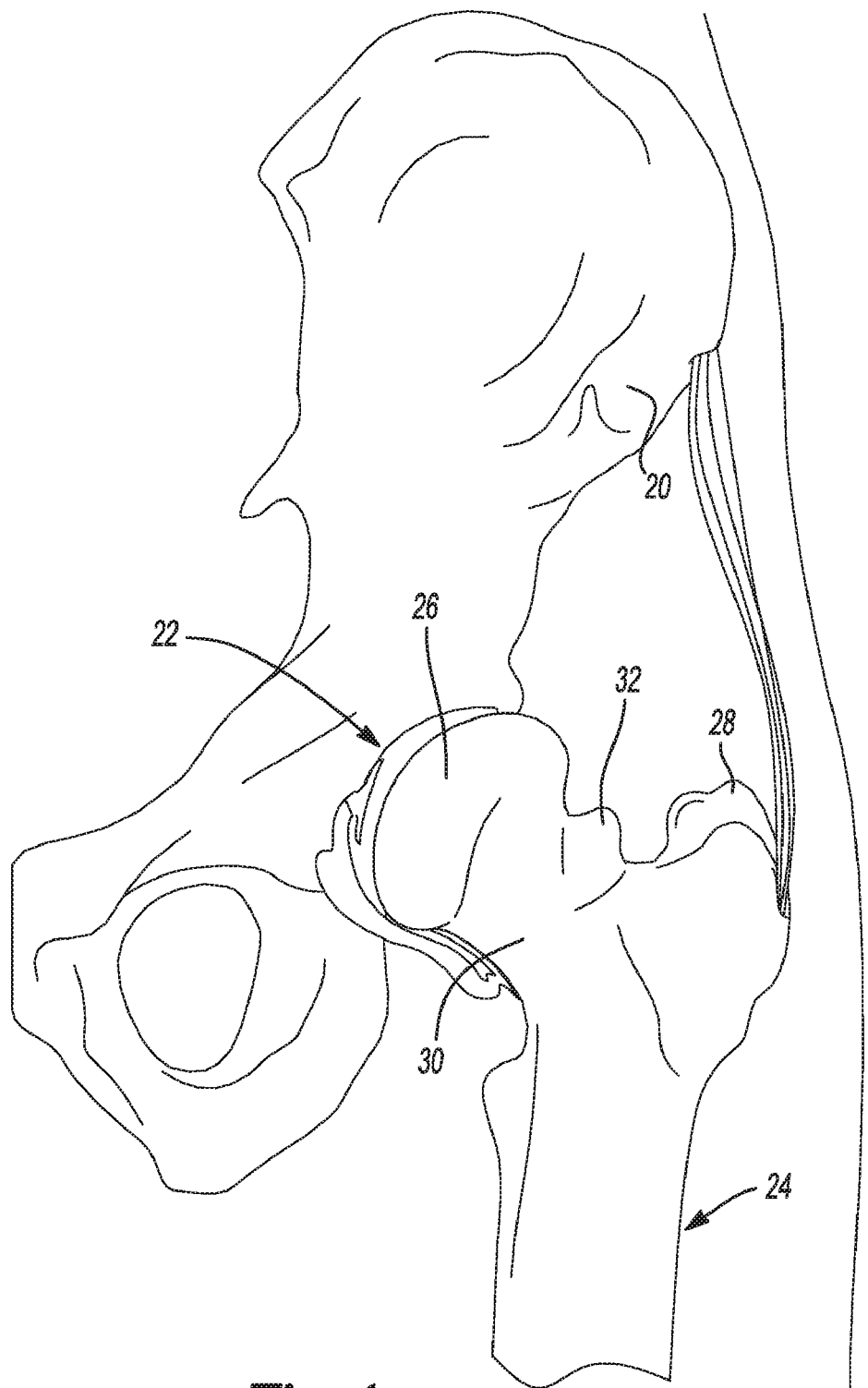
FIG. 1 is a detail environmental view of a patient with an identified femoral articulation range limitation.

With reference to FIG. 1, an anatomy of a single specific patient (SSP) can include a pelvis 20 that defines an acetabulum 22. A femur 24 can articulate within the acetabulum 22. Generally the femur 24 can include a femoral head 26 that defines an articular surface that articulates with the acetabulum 22. A greater trochanter 26 extends from the femur 24 and generally allows for soft tissue attachment to the femur 24. Extending between the greater trochanter 28 and the head 26 is a femoral neck 30. The neck 30 allows the head 26 to be positioned within the acetabulum 22 while the greater trochanter 28 and the body of the femur 24 is positioned away from the pelvis 20 to allow for a range of movement of the femur 24 relative to the pelvis 20. The femoral neck 30, however, may include a defect or bone abnormality 32. The bone abnormality 32 can be congenital or develop over time due to disease or injury. Regardless, the defect or abnormality 32 can impinge upon the acetabulum, such as near a rim or edge (e.g. a high portion 400 in FIG. 9) of the acetabulum 22, to limit a range of motion of the femur 24 relative to the pelvis 20. The range of motion of the femur 24 relative to the pelvis 20 can be one that substantially limits motion of the femur 24 relative to the pelvis 20 or one that causes discomfort in a range of motion of the femur 24 relative to the pelvis 20.

Figure 2:
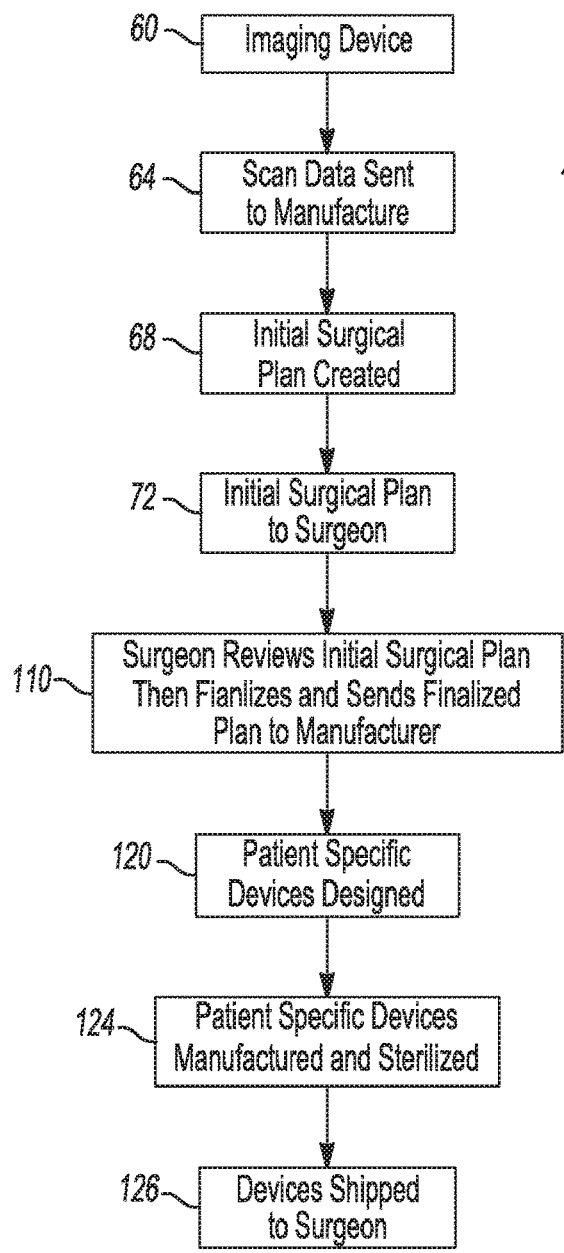
FIG. 2 is a flowchart illustrating a method of preparing a selected patient-specific guide system, according to various embodiments.

Regardless, the bone abnormality 32 can be selected to be removed. In a procedure, a surgeon can obtain access to the patient's anatomy, such as through an incision, and through the surgeon's skill and experience, selectively remove a portion of the bone abnormality 32. Exemplary procedures are disclosed in Beaule, Paule et al., The Young Adult With Hip Impingement: Deciding on The Optimal Intervention, The Journal of Bone and Joint Surgery, Volume 91-A, #1, page 210-221, January 2009, incorporated herein by reference. As disclosed herein a femoral articular impingement can be cured or relieved by removing a portion of the bone defect 32 as planned by a surgeon and with a patient-specific device regarding a single specific patient (SSP). The patient specific device can assist in removing a selected portion of the anatomy to achieve a selected or proposed result on the SSP. As described further herein, as illustrated in FIG. 2, a procedure 50 can be followed to obtain specific information of the SSP, plan a procedure, design patient-specific devices for achieving the procedure, and selecting an appropriate result. Accordingly, the procedure 50 illustrated in FIG. 2 can be used to generate patient-specific devices to achieve a patient-specific result as selected by a user.

Referring to FIG. 2, in preoperative planning, imaging data can be obtained of a selected portion of the SSP including an entire leg, further including a joint to be reconstructed at a medical facility or doctor's office, at block 60. The imaging data can include a detailed scan of a hip, knee and ankle. The imaging data can be obtained using MRI, CT, X-Ray, ultrasound or any other imaging system. In some cases, the scan may be performed with the SSP wearing an unloader brace to stress the ligaments. The scan data obtained can be sent to a manufacturer, at block 64. The scan data can be used by the manufacturer to construct a three-dimensional (3D) image of the selected joint. The 3D image or 3D image data can be used to generate a 3D model that can be used to design and manufacture patient specific devices, as discussed herein. Generally, and depending on the procedure, an initial fitting, guiding, and alignment protocol detailing the fit of any implant components and/or various alignment, milling, reaming and cutting instruments can be prepared. The fitting and alignment protocol can be stored in any computer storage medium (including a local or networked hard disk drive or other stable or temporary storage medium), in a computer file form or any other computer or digital representation. The initial fitting and alignment protocol can be obtained using standard alignment methods or using alignment methods provided by or based on the preferences of individual surgeons.

As discussed above, in the preoperative planning stage of a surgical procedure, multiple image scans of portions of the SSP's anatomy related to the procedure are obtained. Image markers visible in the scan can be placed on the SSP's anatomy to allow image scaling and orientation. The obtained scans of the desired anatomy can be correlated to one another to reconstruct an image of the patient's specific anatomy in three-dimensions.

The outcome of the initial fitting is an initial surgical plan created at block 68 that can be printed or represented in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review, at 72 (and viewable as a computer display 80 in FIG. 3). Using the interactive software, the surgeon can manipulate the position of images of various implant components (when used) and/or alignment/milling/reaming guides or other instruments relative to an image of the joint. Other modifications can include range of movement selections or general sizes and interactions of anatomical portions of the SSP. The surgeon can modify the plan and send it to the manufacturer with recommendations or changes. The interactive review process can be repeated until a final, approved plan is sent to the manufacturer, at 110.

Once the imaging scan has been used to collect scan data, including imaging scan data, in block 60 and, as discussed above, the initial surgical plan is sent to the surgeon in block 72. The initial surgical plan can be viewed as illustrated in FIG. 3A. In FIG. 3A, a screen image 80 is illustrated. The screen image 80 can include selected information such as a surgeon's name, patient name, and other surgeon and patient-specific information. A portion of the screen 80 can include a first block or screen block 82 that describes a proposed femoral head diameter. A second screen block 84 can illustrate a proposed minimal femoral neck diameter. A third screen block 86 can describe a reamer or reamer size to be used.

The reamer to be used can include a radius size of the reaming portion or head of the reamer. The reamer size can be equal to a portion of the Head-to-Neck offset. The Head-to-Neck offset can be the difference between the diameter of the head and the diameter of the neck of the femur to be resected. The size of the reamer can be about one third to about two thirds, including about one half of the value of the difference. As an example, the diameter of the head may be 40 mm and the diameter of the neck may be 24 mm, therefore the difference is 16 mm. The reamer size can be about one half the difference, or about 8 mm as illustrated in block 86.

The computer screen 80 can also include a fourth screen block 88 that illustrates an a angle 90. The a angle 90 can be an angle between a line 90*a* from a center of the femoral head 26 down a center of the femoral neck 30 (e.g. the long axis of the femoral neck) to a line 90*b*. The line 90*b* can be defined between the center of the femoral head 26 and an intersection of a circle defined by the center of the femoral head 26 having a radius from the center to an edge of the spherical portion of the femoral head and where the circle intersects a non-spherical portion of the femoral head 26 by the femoral neck. The a angle 90 can be used to illustrate a range of motion of the SSP after the initially proposed plan in block 72 and illustrated on screen 80.

In a fifth screen block 94, a center edge angle 96 is illustrated. The center edge angle 96 is an angle between a first line 96*a* that extends from a center of the femoral head 26 to a superior rim of the acetabulum 22 and a second line 96*b* extending from the center of the femoral head 26 substantially parallel with the long axis of the femur 24 or a mechanical axis of the anatomy. The center edge angle 96 can also be used to assist in determining or designing various guide members, as discussed herein.

Finally, a sixth screen block 98 can illustrate a range of motion, from various perspectives, for viewing by the surgeon based upon a modification of the SSP with the initially proposed plan or procedure and the instruments designed therefrom. Accordingly, the screen 80 is a representation of the initial surgical plan sent to the surgeon in block 72. The initial surgical plan, as discussed above, is based upon the scan data sent to the manufacturer in block 64.

The six screen blocks 82-98 can be used to describe information received based upon the imaging scan data sent to the manufacturer in block 64 and information based upon the suggested or initially suggested sizes to achieve a selected range of motion within the SSP after the selected procedure. With continuing reference to FIGS. 2 and 3, the surgeon can finalize, including changing and altering the initial plan, and sending the plan to the manufacturer in block 110 of the procedure 50. The surgeon can alter the plan by changing the a angle 90 in screen block 88 and the center edge angle in screen block 94. The two angles can be altered by inputs from the surgeon directly into a computer file that is included or that generates the screen 80 or sent separately for consideration by the manufacturer. Additionally, the specific size or positioning of various portions of the instruments, such as discussed herein including a reamer guide, can be altered by the surgeon when finalizing the initial plan. The surgeon can then send the finalized plan to the manufacturer in block 110.

Figure 3B:
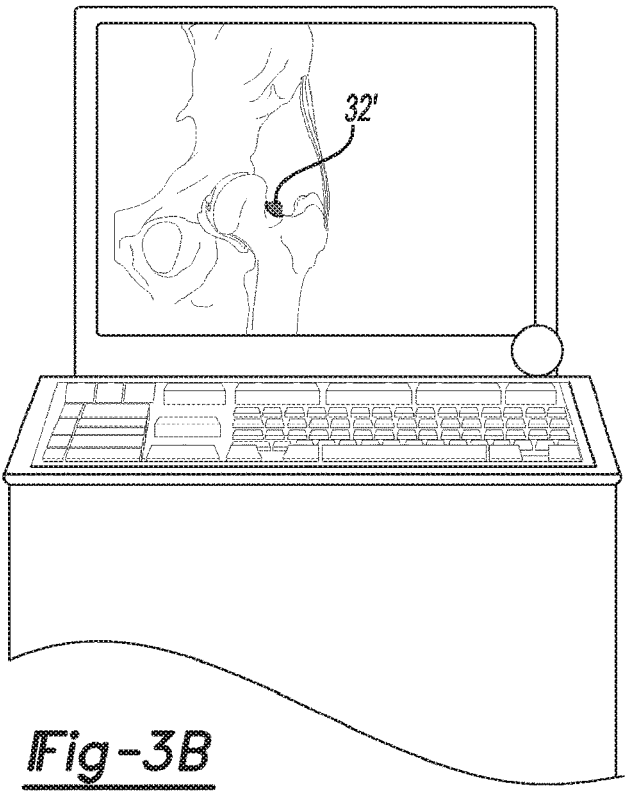
FIG. 3B is a view of a display device illustrating image data of a patient with a region to be removed.
Figure 3A:
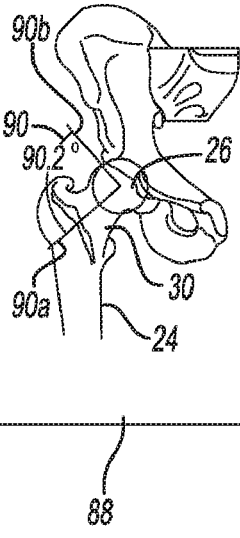
FIG. 3A is a surgeon input screen, according to various embodiments.

According to various embodiments the screen image 80 of a display device can also illustrate the image data of the patient with a planned removal region 32' illustrated, for example, with shading or varying colors as shown in FIG. 3B. The planned removal region 32' can relate to the defect 32 or any appropriate region to be removed based upon the finalized plan. It is also understood that the planned removal region 32' may be shown to change based upon variations in the planning. The planned removal region 32' can be used to design and manufacture any appropriate device, as discussed further herein.

Various methods of sending the initial and final surgeon-approved surgical plans can be used. The surgical plans can be, for example, transferred to an electronic storage medium, such as CD, DVD, flash memory, which can then be mailed using regular posting methods. In various embodiments, the surgical plan can be e-mailed in electronic form or transmitted through the internet or other web-based service.

Based upon the finalized plan in block 110, patient-specific devices are then designed in block 120. The patient specific devices can include patient-specific alignment/milling/reaming or other guides. The patient specific devices for the SSP's joint can be developed using a CAD program or other three-dimensional modeling software, such as the software provided by Materialise, for example, according to the surgical plan, at 120.

Patient-specific guides can then be manufactured and sterilized at 124. The guides can be manufactured by various stereolithography methods, selective laser sintering, fused deposition modeling or other rapid prototyping methods. In some embodiments, computer instructions of tool paths for machining the patient-specific guides can be generated and stored in a tool path data file. The tool path can be provided as input to a CNC mill or other automated machining system, and the alignment guides can be machined from polymer, ceramic, metal or other suitable material. Patient-specific devices are defined as those constructed by a surgical plan, such as the finalized pan, approved by the doctor using three-dimensional images (including 3D models based on the image data) of the SSP's anatomy and made to closely conform and mate substantially as a negative mold to corresponding portions of the patient's anatomy, including bone surfaces with or without associated soft tissue, such as articular cartilage, for example.

Images of the hip joint anatomy of the joint surface of the proximal femur with or without the associated soft tissues, such as articular cartilage, on the respective bone surfaces can be used in the alignment procedure. The alignment procedure can include, for example, the selection of an anteversion angle, a femoral neck angle and other orientations for positioning a femoral implant, such as a resurfacing component, without notching or impinging on the femoral neck. Multiple alignment procedures can be provided to accommodate the experience and preference of individual surgeons. For example, the alignment procedure can be based on the anatomic and mechanical axes. Further, the alignment procedure can be deformity-specific in relation, for example, to various deformities and/or malformations of the hip joint anatomy, articulation and orientation.

The sterilized devices can be shipped to the surgeon or medical facility, at 126 for use during the surgical procedure. The sterilized devices, therefore, can be included in a single kit 450 (FIG. 10) for delivery to a user, such as a surgeon, as a single unit. The sterilized devices also need not be kept in inventory at a place of use, but can be manufactured and shipped on demand for a particular procedure on the SSP. It is also understood, that the patient specific devices need not be sterilized prior to shipping, but that prior sterilization can decrease later processing at a facility of use of the patient specific devices.

Figures 4A, 4B:
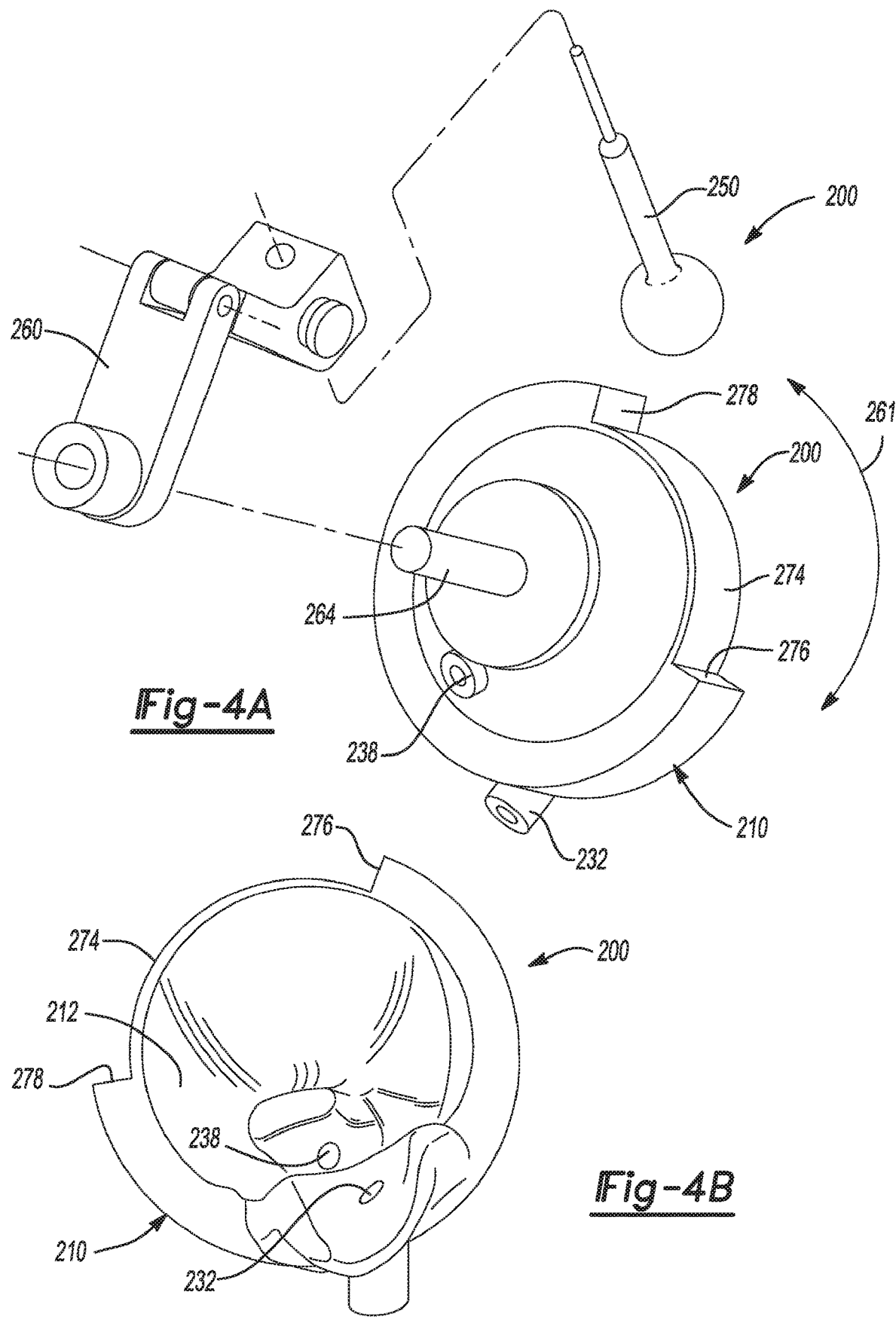
FIG. 4A is a perspective exploded view of a reamer guide, according to various embodiments.
FIG. 4B is an interior perspective view of the reamer guide.
Figure 5:
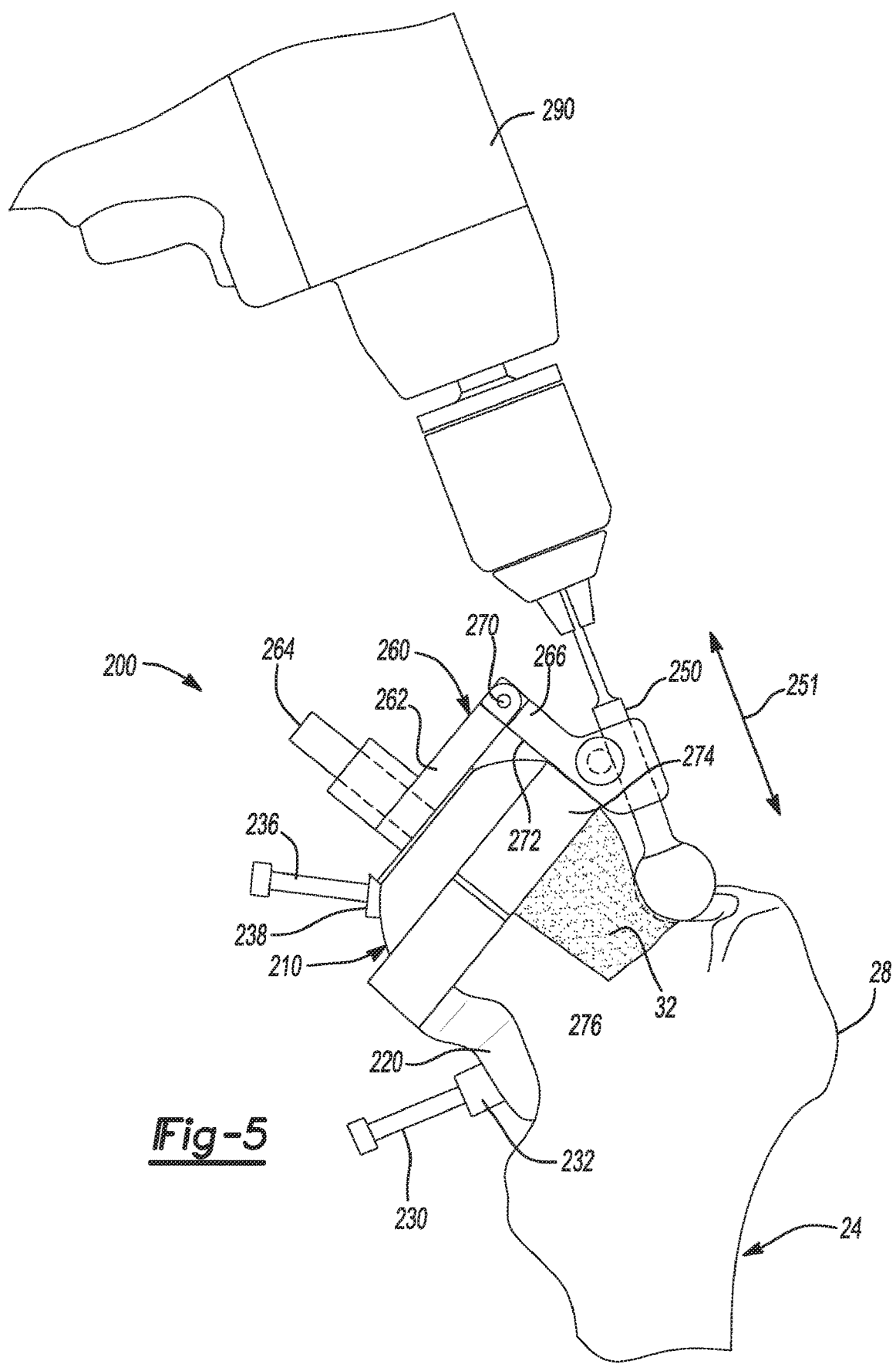
FIG. 5 is an environmental view of the reamer guide.

One of the patient specific devices to achieve the finalized plan from block 110 (including alignment and/or range of motion) can include a femoral neck reamer guide 200, as illustrated in FIGS. 4A, 4B, and 5. The femoral reamer guide 200 can be one of a plurality or the only patient-specific device designed, manufactured, and shipped (blocks 120, 124, and 126) based upon the plan 50. Nevertheless, the portions of the neck reamer guide 200 are discussed herein.

Initially, the neck reamer guide 200 can also be referred to as a milling guide. Generally, the neck reamer guide 200 includes femur contacting portion. The femur contacting portion can include a reamer cap or dome portion 210 that includes a reamer interior or bone contacting surface 212 that substantially mates with an articular portion of the femoral head 26 based upon the scan data sent to the manufacturer in block 64 of the procedure 50. The interior surface 212 of the reamer guide 200 can include contours and geometries that substantially mirror or form a negative relative to the shape of the articular surface of the femoral head 26. Accordingly, the interior surface 212 can mate substantially tightly or nest substantially tightly and in substantially only one configuration with the femoral head 26 of the SSP. In other words, the reamer interior surface 212 can be designed and manufactured to engage the femoral head of substantially only the SSP in a manner appropriate for guiding a reamer, as discussed herein.

Various portions can extend from the dome portion 210. A neck extension finger 220 that extends along the neck 30 of the femur 24 and can also extend down a portion of the shaft of the femur 24, if selected, can extend from the dome 210. The extension finger 220 can assist in further conformational holding of the reamer guide 200 relative to the femur 24. Thus, the finger 220 can include an anatomy contacting surface that mirrors or is a negative of a selected portion of the femur 24.

To assist in holding the reamer guide 200 relative to the femur 24, pins or screws can engage the femur 24. For example, a first screw 230 can pass through a first passage 232 in the extension finger 220 and engage the femur 24. The screw 230 can extend at an angle that would pass towards the greater trochanter 28 of the femur 24. Additionally, a second screw 236 can pass through a second passage 238 of the done 210 and engage a fovea capitis of the femoral head 26. Generally, the fovea capitis can be engaged with a screw without substantially damaging the articular region of the femoral head 26 due to the tissue attachment of the ligament teres between the femur 24 and the pelvis 20 within the acetabulum 22.

Accordingly, at least two screws 230 and 236 can be used to further fix the reamer guide 200 to the femur 24 of the SSP. Nevertheless, the femoral reamer guide 200 will substantially mate with the femur 24 of the SSP in substantially only one configuration or position due to the patient-specific device nature of the reamer guide 200, which was designed and manufactured based upon the scan data sent to the manufacturer in block 64. Thus, the guide 200 that is designed to assist in performing or carrying out the finalized plan procedure sent to the manufacturer in block 110 can ensure the completion of the procedure based upon the finalized plan due to the patient-specific device nature of the guide 200 because the guide 200 will engage the femur 24 of the SSP in substantially one configuration to guide a mill or reamer instrument 250 in substantially a single manner or path, as discussed herein.

The reamer instrument 250 that is guided with the guide body 200 is positioned with an arm or member 260 that can include a first portion 262 that extends from a pin or post 264. The pin 264 can extend from the dome portion 210 of the reamer guide 200 in any appropriate position. The first arm portion 262 can extend from the pin 264 in any appropriate manner to allow for positioning of a second arm portion 266 relative to the defect or bone abnormality 32 of the femur 24 such that the reamer instrument 250 can be guided with the guide 200 relative to the defect 32, generally in the direction of arrows 251 and 261, as discussed herein. The second arm portion 266 can be moved relative to the first arm portion 262, such as via an articulation or pin connection 270. The first arm portion 262 can be formed to be substantially rigid as can the second arm portion 266.

The articulating connection 270, therefore, can allow the second arm portion 266 to include a guide engaging surface 272 to contact a guide surface 274. The guide surface 274 can be formed with the reamer guide 200 to allow the second arm portion 266 to glide or move along the guide surface 274 to allow positioning of the reamer instrument 250 relative to the bone defect 32 in a manner according to the finalized plan sent to the manufacture in block 110. The guide surface can further include at least a first stop surface 276. The second guide arm portion 266, therefore, can move along the guide surface 274 until it engages the first stop 276. The guide 200 can further include a second stop portion 278.

Accordingly, the reamer guide 200 can define an arc, shown as arrow 261 that defines a range of movement of the second arm portion 266 relative to the pin 264. Thus, the guide arm 260 can guide the reamer instrument 250 along the arc 261 to remove the bone defect 32 in a selected manner. The reamer can also move in the direction of arrow 251 generally axially within the arm 260. An angle, length, and other geometric features of the arc 261 and the length of position of the arrow 251 relative to the defect 32 and the other portions the femur 24 can be designed based upon the finalized plan sent to the manufacturer in block 110, which is initially based upon the scanned data sent to the manufacturer in block 64. Accordingly, the reaming configuration that is defined by the guide surface 274, the two stops 276 and 278, the position of the pin 264, the configuration of the first arm portion 262 relative to the pin 264 and the articulation connection 270 and the surface 272 of the second arm portion 266 all cooperate to ensure an appropriative configuration of movement of the reaming or milling instrument 250 relative to the femur 24. As discussed above, the guide 200 is positioned relative to the femur 24 in substantially a single configuration or position due to the patient-specific nature of the reamer guide 200. Thus, the reaming of the defect 32 of the femur 24 is also substantially patient-specific to the SSP to ensure a selected result based upon the scanning data.

The reamer instrument 250 can be powered by any appropriate instrument, such as a drill motor 290. The drill motor 290 can be powered or operated by a surgeon to power the milling instrument 250 during the milling or reaming procedure. The movement of the reamer instrument 250, however, relative to the guide 200, can be based upon a force provided by the surgeon by moving the guide arm 260 along the surface 274 and between the two stops 276 and 278.

According to various embodiments, a lateral femoral neck reamer guide 200' can also be provided or be provided as an alternative to the femoral neck reamer guide 200. The lateral femoral neck reamer guide 200', as exemplary illustrated in FIGS. 5A' and 5B' can include portions that are similar to the femoral neck reamer guide 200 and these portions can include the same reference numerals augmented by a prime. Generally, the lateral femoral neck reamer guide 200' can include a guide portion 210' that is able or formed to contact or be positioned near a lateral portion of the femur 24, such as near the greater trochanter (which is show resected in FIG. 5A' as discussed further herein) and/or a shaft 24a of the femur 24.

The lateral femoral neck guide 200' can also be the defect reamer guide, as discussed above and herein. The lateral guide 200', however, can be affixed to a lateral surface of a portion of the femur 24. For example, the lateral guide 200' can include a first extension portion 201' that can extend along a portion of a shaft 24a of the femur 24. A guide or guiding portion 210' can also be positioned relative to a lateral portion of the femur 24, and contact a portion of the shaft 24a or a portion of the greater trochanter 28 or resected greater trochanter, as illustrated in FIG. 5A'. Nevertheless, the lateral reamer guide 200' can include portions similar to the reamer guide 200, as discussed above, and be designed to resect a portion of the femoral neck 30, including the defect 32.

The lateral guide 200' can include also include a bone contacting surface 212' that is an interior surface, as illustrated in FIG. 5B'. The bone contacting surface 212' is formed to include contours that substantially match at least a portion of the femur 24, such as a lateral surface of the femur 24a and the greater trochanter 28. The bone contacting surface 212' can extend along the shaft portion 201' and in the trochanter contacting portion 210'. The contours can substantially match or form a negative or mirror image of the femur 24 to assist in positioning the lateral reamer guide 200' relative to the femur 24 for resecting the femur 24, according to the final plan. Accordingly, the lateral guide 200' can be positioned relative to the femur 24 to position a reamer for reaming the defect 32 according to a process similar for the guide 200, as discussed above.

The lateral reamer guide 200' can further include holding portions or fixing portions. A first screw 230' can pass through a first passage 232' and a second screw 236' to pass through a second passage 238'. The screws or other fixation portions can assist in fixing the lateral guide 200 relative to the femur 24 during guiding of the reamer 250 relative to the femur 24.

Additionally, extending from the dome or guiding portion 210' can be a pin 264' that can engage a portion of a guide arm 260' to allow the guide arm 260' to generally move in at least a portion of an arc 261' defined by the guide 200'. Similar to the guide 200, discussed above, the guide 200' can include a guide surface 274' and a second guide arm portion 266' can include a guide surface to engage the guide surface 274' of the guide 200'. A first arm portion 262' can extend an engage the second arm portion 266' at a hinge or flexing portion that can include a connection pin 270'.

The second arm portion 266' can also include a holding or guiding portion to hold the reamer 250 and also allow the reamer 250 to move axially generally in the direction of arrow 251' relative to the second guide arm portion 266' and the guide 200'. Accordingly, the guide 200' including or in operating the guide arm 260 can move or guide the reamer 250 for reaming a selected portion of the femur 24, such as the defect 32. It will be understood that the reamer 250 can be powered with a drill motor 290, as discussed above.

Additionally, the position of the guide surface 274' can be developed based upon the final plan as discussed above. The guide surface 274' can also be stopped or limited by first and second stop portions 276' and 278'. The stop portions 276' and 278' limit movement of the second guide arm 266' along the guide surface 274' so that the guide arm 260' moves relative to the femur 24 based upon the design of the lateral guide 200' to resect the defect 32 or selected portion of the femur 24 based upon the final plan.

Accordingly, it will be understood, that the reamer 250 can be guided relative to the femur 24 with a selected patient specific guide or defect guide that can be positioned relative to the femur 24 in an appropriate manner. For example, the guide 200 can be positioned over the femoral head to guide the guide arm 260 relative to the femur 24. In addition, or alternatively thereto, the lateral guide 200' can be positioned in a lateral portion of the femur 24 to guide the reamer 250 relative to the femur 24. It will be further understood that based upon a selected resection, two resection guides may be selected to achieve a selected amount of resection femur 24. For example, if a plurality of cuts or a complex angle is required or selected to resect the femur 24 in a selected manner, a plurality of the guides can be positioned on the femur 24 in a plurality of positions to achieve the selected resection.

As an alternative to the reamer guides 200, 200' discussed above, a patient specific bone removal template 299, as illustrated in FIGS. 6-8, can be designed and manufactured to instruct a surgeon on the bone to be removed from the femur 24. As discussed above, the femur 24 can include the defect 32 that can be modeled and/or determined in the image data as the region to be removed 32'. The region to be removed 32' can be used to generate a 3D model and further used to instruct (e.g. via a CAD model for manufacturing) a milling or 3D manufacturing machine to manufacture the template 299 based on the determined region to be removed 32'

The template 299 can include a handle portion 301 to allow for grasping by a user, such as a surgeon. The handle 301 can interconnect with a template region 302 that has been specifically designed to match a patient and to indicate tissue to be removed. As discussed above, the bone removal region 32' can be based upon the defect 32 of the femur 24. According to various embodiments, the template region 302 of the template 299 can be an inverse of the bone removal region 32' such that when the bone removal region 32' has been removed from the femur 24 that the template region 302 will contact the remaining femur portion 24 to substantially mimic the region to be removed 32'. To assist in reference or determining an appropriate amount of removal, reference fingers or tangs 304a-304d, can also be provided to engage regions of the femur 24 that are not intended to be removed. For example, the tangs 304a and 304b can contact regions of the neck 30 or the head 26 while the fingers 304c and 304d can contact regions around the greater trochanter 28. The template region 302, therefore, can be positioned to contact the femur 24 during portions of the bone removal procedure to assist the surgeon in determining whether an appropriate amount of bone has been removed.

With continuing reference to FIG. 6 and additional reference to FIGS. 7 and 8, a reamer 306 can be powered by a drill motor 308 that is operated by the surgeon to remove the bone defect 32. The reamer 306 can be operated to remove the bone defect 32 in incremental portions, such as about 1 or 2 mm layers per pass, such that the template 299 can be contacted to a bone resection region 32a after each pass or at a selected time to ensure that the selected amount of bone has been removed. It is understood, however, according to various embodiments, that a surgeon can determine that additional or less bone can be removed intraoperatively and uses the template 299 as a guide. As illustrated in FIG. 7, after a selected period of time, the template 299 can be contacted near the bone resection region 32a.

As illustrated in FIG. 7, if the template 299, including the template region 302 does not rest appropriately, such as flushly, with the surrounding bone surface around the bone resection region 32a, then resection can continue with the reamer 306 by the surgeon. After an additional portion of resection, the template 299 can be placed adjacent the bone resection region 32a again, as illustrated in FIG. 8, to confirm that the template region 302 of the template 299 rests substantially adjacent and/or in contact with the surrounding bone. Again, the positioning tangs 304a-d can be used to assist in confirming positioning of the template 299 relative to the adjacent portions of bone to ensure that the template region 302 is in the selected and appropriate position.

The template region 302 is based upon the determination of the region to be removed 32' determined in the plan 50, discussed above. Accordingly, the device designed in block 120 can be the template 299 that is based upon the final surgeon plan in block 110. The template region 302 can be based upon the determination of the volume and position of bone that needs to be removed or is determined to be removed to achieve the selected movement of the femur 24. Accordingly, the template 299 can contact the bone at the bone resection region 32a to assist in confirming and determining an appropriate amount of bone to be removed.

It is understood that an opening or incision in the patient can allow for access to the femur 24 with the template 299 and that the same or different opening can be used to allow access of the reamer 306 to the femur 24 for resection. Accordingly, the bone can be resected at an appropriate rate and time until the template region 302 of the template 299 contacts the bone appropriately, such as flushily or with a determined clearance or contact amount. It is also understood that the template 299 can be used in conjunction with either of the guides 200 or 200' discussed above to ensure an appropriate amount of the bone has been removed. Accordingly, once the selected guide 200 or 200' has been used to resect an appropriate or selected portion of the bone, the template 299 can be used to confirm or fine tune any selected resection.

A second type of a patient specific device can include a greater trochanter guide 370 as illustrated in FIGS. 9 and 10. Accordingly, the trochanter guide 370 is a patient-specific device. The trochanter guide 370 can be designed and manufacturer based upon the scanned data sent to the manufacture in block 64 and the finalized plan sent to the manufacturer in block 110. The trochanter guide 370, therefore, can substantially mate with and contact a specific anatomy, including the greater trochanter 28 of the femur 24 of the SSP. Illustrated in FIGS. 9 and 10 is the femur 24 with no soft tissue surrounding the femur 24. It is understood by one skilled in the art, however, that soft tissue can be connected to the greater trochanter 28 as illustrated in FIG. 1. To allow for positioning of the reamer guide 200 on the femoral head 26, the greater trochanter 28 can be resected from the remaining portions of the femur 24 prior to dislocating the femur 24 from the acetabulum 22. The soft tissue connected to the greater trochanter 28, therefore, need not be stretched or moved substantially relative to the pelvis 20 and the acetabulum 22 when dislocating the femur 24 from the acetabulum 22 to perform the resection on the femur 24 and a resection to the acetabulum 22, as discuss further herein. Additionally, the greater trochanter guide 370 can be used to guide fixation pins or screw holes into the greater trochanter 28 relative to the femur 24 for reattachment of the greater trochanter 28 to the femur 24 after resecting the bone defect 32.

The trochanter guide 370 can include any appropriate size or area to contact the femur 24. Generally, the trochanter 370 can include a bone contacting surface 372 to contact the femur 24 in a substantially patient-specific manner. The contact surface 372 of the trochanter 370 can include a geometry that is substantially a mirror image or a negative of a portion of the femur 24. Accordingly, the trochanter guide 370 that is a patient-specific device can contact the SSP in substantially a single configuration or position to allow for resecting the greater trochanter 28 in a single selected manner. Generally, the mating and nesting of the greater trochanter 370 relative to the femur 24 is enough to maintain positioning of the trochanter 370 relative to the femur 24 for the resection and drilling procedures.

Once the access is made to the femur 24, the greater trochanter guide 370 can be positioned on the femur 24, as exemplarily illustrated in FIGS. 9 and 10. A plurality of bores, as exemplarily illustrated as three bores, can be drilled through three drill guide passages 374, 376 and 378 in a drill guide section 380 of the trochanter guide 370. The drill guide 380380 can allow for the drilling of passages 382, 384, and 386 through the greater trochanter 28 and through the remaining portion of the femur 24. Generally, the passages 382, 384, and 386 can be substantially through the femur 24 to allow for a purchase of a screw or a bolt into cortical bone that is substantially opposite the beginning or entry of the passages into the greater trochanter 28. The passages 382-386 can generally extend from the greater trochanter 28 to within the region 388 of the femur 24 generally near, such as slightly superior, the lesser trochanter 390.

After resection of the greater trochanter and resection of the bone defect 32, the greater trochanter 28 can then be reattached to the femur 24 with appropriately length screws or bolts. The passages 382-386 can be used to substantially precisely reattached the greater trochanter 28 to the femur 24. The lengths of the screws can also be determined prior to the procedure based upon the scan data sent to the manufacture in block 64. In determining the length of the screw prior to the procedure only an appropriate length screw can be provided as a portion of the patient-specific kit. Also, intra-operative measuring may not be necessary to ensure appropriate fixation of the screws through the greater trochanter 28 and into cortical bone substantially opposite the greater trochanter 28. Also, the number of screws may be limited in the kit as only one length can be provided, thus reducing cost per kit or cleaning of unused screws after a sterile seal is broken.

Once the screw passages 382-386 are drilled into the femur 24, a resection of the greater trochanter 28 can be performed at a substantially preplanned and precise position by using a cut guide slot 392 formed into the greater trochanter guide 370. The trochanter cut guide slot 392 can be positioned relative to the femur 24 based upon the patient-specific nature of the greater trochanter guide 370 to ensure an appropriate resection of the greater trochanter 28. An appropriate resection can include substantially no resection or limited disruption of any soft tissue connected to the greater trochanter 28, while ensuring an appropriate amount of bone in the resection to allow for an appropriate reattachment of the greater trochanter 28 to the femur 24. An appropriate instrument can be used to perform the resection such as a saw blade, including a reciprocating saw generally understood by one skilled in the art. An appropriate saw can include a reciprocating saw blade generally used for bone resection as generally understood by one skilled in the art. Once the resection of the greater trochanter 28 is completed, the trochanter guide 370 can be removed from the femur 24. Additionally, once the greater trochanter 28 is resected, the femur 24 can be dislocated from the acetabulum 22. Once the femur 24 is dislocated from the acetabulum 22, the defect milling guide 200 and/or 200' can be connected to the femur 24 and/or femoral head 26 to allow for a resection or removal of the selected bone defect 32.

With reference to FIGS. 11 and 12, the acetabulum 22 can also be a portion of the diagnosis of the femoral acetabulum impingement on the femur, such as on the defect 32, can be determined. For example, a rim or upper portion or exterior portion of the acetabulum 22 can include portions that are substantially high relative to an internal portion of the acetabulum. A high rim portion 400 can extend beyond a low rim portion 402, relative to each other, and relative to a deep or internal portion of the acetabulum 22. The high rim portion 400 can be a distance 401 higher than an upper rim portion 420 of the acetabulum guide 410. Accordingly, an acetabulum cut guide 410 can be patient specific device as designed and manufactured to be seated or positioned within the acetabulum 22.

The acetabulum cut guide 410 can include the upper rim portion 420 that is connected to a central deep or low portion 422 with spokes or extension arms 424. It is understood that the acetabulum cut guide 410 can also be substantially solid rather than including a plurality of connection spokes 424, but the connection spokes that define the open areas 426 can assist in minimizing material, weight, and impingement on articulation portions of the acetabulum 22.

The acetabulum cut guide 410 can include a bone contacting surface defined at least by an exterior surface 430 of the extending spokes, an exterior surface 432 the rim 420, and an exterior surface 430 of the central portion 422. The bone contacting surfaces 430, 432, and 434 allow the acetabulum cut guide 410 to be positioned within the acetabulum 22 of the SSP in a substantially single configuration and position. Again, the geometry or configuration of the acetabulum 22 can allow for the design and manufacturer of the cut guide 410 in a substantially single configuration to engage the acetabulum 22 in a substantially single manner. Thus, the acetabulum cut guide 410 can be formed in a patient-specific manner to engage the acetabulum 22 of the SSP in a substantially single configuration.

Once the patient-specific acetabulum cut guide 410 is positioned within the acetabulum 22 of the SSP, an instrument can be used to engage an upper or cut guide surface or guide surface 440 of the rim 420. As the cutting or reaming instrument engages the upper surface 440 of the rim 420, the high regions 400 from around the acetabulum 22 can be removed. Thus, the upper edge or rim of the acetabulum 22 can be substantially minimized to achieve an appropriate range of motion of the femur 24 relative to the pelvis 20.

Accordingly, the reamer guide 200 and the acetabulum cut guide 410 can be formed in a substantially patient-specific manner including various configurations and materials as discussed above. The defect reamer guide 200 and the acetabulum cut guide 410 can be used individually or together to achieve the planned range of motion in the SSP. It will be understood that in selected patients, only the bone defect 32 reduces or minimizes the range of motion of the femur 24 relative to the pelvis 20. Accordingly, in various patients the finalized plan sent to the manufacture in block 110 need not include information that requires resection of a portion of the acetabulum 22. For example, if the Center Edge angle 96 is determined to be within an appropriate range, such as greater than about 40 degrees, an acetabular reamer guide 410 may not be necessary and therefore, not designed or provided. Nevertheless, the finalized plan sent to the manufacturer in block 110 can include information for forming or designing the defect reamer guide 200 and the acetabulum resection guide 410 to achieve a selected range of motion of the femur 24 relative to the pelvis 20. Additionally, the greater trochanter guide 370 can be designed in the patient-specific manner as discussed above, to allow resection of the greater trochanter to minimize or reduce any stretching of soft tissue connected to the trochanter during dislocation of the femur 24 to position the mill guide 200 relative to the femoral head 26.

As discussed above, all of the guides, including the reamer guide 200, the template 299, the greater trochanter guide 370, and the acetabular resection guide 410 can be formed of materials that are relatively inexpensive, and can be used for a single procedure on the SSP. Generally, the guide patient-specific devices can be used on the SSP in performing the planned procedure and then discarded. In discarding the patient-specific devices, it can be ensured that the patient-specific devices are specific to the SSP to achieve a planned result. Additionally, chances of cross contamination from one patient to another due to reuse of the instrument can be substantially eliminated. Additionally, a requirement of maintaining a selection and inventory of instruments and guides and labor and instrumentation for cleaning instruments and guides is not required by a facility. Generally, the patient-specific devices can be formed for each procedure based upon the data provided to the manufacture that is based on the SSP and then the patient-specific devices can then be discarded.

It is also understood that all of the guides 200, 200', 370, and 410 along with the template 299 can be provided to together as a single kit 450 to the surgeon, along with the ancillary portions including the reamer 250 and pins 230 and 236. Also, the kit 450 can include any implants, such as screws 452 to fit in the passages 382-386. Thus, the entire kit 450 can be provided to a surgeon as illustrated in FIG. 13. The kit 450 can be sterilized and sent to the surgeon in block 126. It will be further understood, however, that the kit 450 need not include all portions. For example, the kit 450 may only include one of the femoral defect guides 200, 200', or 299. In an alternative the kit 450 may include at least two or three of the guides for selection by the surgeon intraoperatively of the guide and/or template to be used. Also, the kit 450 may not include the acetabular guide 410. IN addition, the kit need not include the greater trochanter cut guide 370. For example, the surgeon may free hand cut the greater trochanter 28. If the greater trochanter guide 370 is not included, the screws 452 can be included for use in fixation of the resected greater trochanter 28 even if resected without the guide 370. Thus, some portions are optional, but may also be included in the kit 450.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to resect a selected portion of an anatomy to improve a range of motion of a femur relative to a pelvis in a specific patient, comprising:
    a patient specific tissue removal template having a template region shaped to an inverse of a predetermined region of tissue to be removed;
    wherein the predetermined region of tissue to be removed is based upon an analysis of the anatomy of the specific patient.

2. The system of claim 1, wherein the patient specific tissue removal template has the template region shaped to match a portion of a determined resection shape at a femoral neck of the anatomy and operable to contact the femur to analyze a resection of the femur.

3. The system of claim 1, wherein the patient specific tissue removal template further includes femur contacting tangs to align the template region relative to the femur of the anatomy.

4. The system of claim 3, wherein the tangs extend a distance from the template region.

5. The system of claim 3, wherein the femur contacting tangs comprise:
    a first tang having a first curved tip to define a first contact edge;
    a second tang spaced from the first tang and having a second curved tip to define a second contact edge; and
    an indentation between the first tang and the second tang to allow the first and second tangs to fit around anatomy of the femur.

6. The system of claim 3, wherein the patient specific removal template comprises:
    a plate defining the femur contacting tangs; and
    a protrusion extending from the plate to define the template region.

7. The system of claim 6, wherein the protrusion extends from the plate a distance equal to a depth of bone to be removed from the femoral neck sufficient to allow articulation of a femoral head within an acetabulum without impingement of the femoral neck.

8. The system of claim 3, wherein the femur contacting tangs comprise:
    a first pair of tangs extending from the template region in a first direction and shaped to contact a femoral head of the femur; and
    a second pair of tangs extending from the template region in a second direction opposite the first direction and shaped to contact a greater trochanter of the femur.

9. The system of claim 1, further comprising:
    a femoral neck resection guide including:
        a bone contacting surface that mates with a surface of the femur;
        an exterior surface opposite the bone contacting surface;
        a pin extending from the exterior surface;
        a guide surface defined by at least a portion of the exterior surface; and
        a guide arm moveably connected to the pin including a guide arm surface configured to contact the guide surface during movement of the guide arm relative to the exterior surface;
        wherein the guide arm includes a mill passage to engage a mill instrument that is configured to resect the selected portion of the femur.

10. The system of claim 1, further comprising:
    a greater trochanter guide including an anatomy contacting surface that is a negative of and operable to contact an anatomy of the specific patient in a substantially single position, wherein the greater trochanter guide includes:
        a cutting guide slot configured to be positioned at a patient specific location relative to the femur of the patient; and
        a drill guide portion operable to orient a drill guide passage at a specific location relative to the femur of the patient.

11. The system of claim 1, wherein the patient specific tissue removal template further comprises a handle portion extending from the template region.

12. A tissue removal template for performing a femoral acetabular impingement procedure on a hip joint, the tissue removal template comprising:
   a handle shaft;
   a base plate comprising:
      a central portion connected to the handle shaft;
      a first contact portion extending from a first end of the central portion to engage a first portion of the hip joint; and
      a second contact portion extending from a second end of the central portion opposite the first contact portion to engage a second portion of the hip joint; and
   a protrusion extending from the central portion opposite the handle to a length sufficient to allow a femoral head to fully articulate within a pelvis of the hip joint.

13. The tissue removal template of claim 12, wherein the protrusion comprises an inverse of a region of tissue to he removed from the hip joint.

14. The tissue removal template of claim 13, wherein the protrusion matches a predetermined region of tissue to be removed that is based upon an analysis of anatomy of a specific patient.

15. The tissue removal template of claim 12, wherein the protrusion is shaped as an inverse of a shape of an abnormality on a neck of the femoral head.

16. The tissue removal template of claim 12, wherein:
   the first contact portion is configured to provide a first pair of point contacts against the first portion of the hip joint, the first portion comprising a femoral head of the hip joint; and
   the second contact portion is configured to provide a second pair of point contacts against the second portion of the hip joint, the second portion comprising a greater trochanter of the hip joint.

17. The tissue removal template of claim 16, wherein the first and second pairs of point contacts each comprise a pair of fingers extending from the central portion.

18. The tissue removal template of claim 16, further comprising:
   a first notch located between the first pair of point contacts configured to provide clearance for a portion of the femoral head; and
   a second notch located between the second pair of point contacts configured to provide clearance for a portion of the greater trochanter.

19. A tissue removal template comprising:
   a bone referencing portion configured to contact unaltered bone landmarks;
   a template portion extending from the bone referencing portion configured to flushly engage a reamed bone surface between the unaltered bone landmarks, wherein the template portion comprises a protrusion having a volume configured to fill a void between the unaltered bone landmarks where a bone abnormality has been removed; and
   a handle shaft extending from the bone referencing portion opposite the template portion.

20. The tissue removal template of claim 19, wherein:
   the bone referencing portion is configured to extend from a femoral head to a greater trochanter of a femur of a hip joint; and
   the protrusion is configured to have a depth between a bone-engaging surface of the protrusion and a plane extending across the bone referencing portion sufficient to allow articulation of the femoral head within an acetabulum of the hip joint without impingement from the femoral neck.

* * * * *

UNITED STATES PATENT AND TRADEMARK OFFICE
CERTIFICATE OF CORRECTION

PATENT NO. : 11,406,398 B2
APPLICATION NO. : 16/584134
DATED : August 9, 2022
INVENTOR(S) : Meridew et al.

Page 1 of 1

It is certified that error appears in the above-identified patent and that said Letters Patent is hereby corrected as shown below:

In the Claims

In Column 17, Line 19, in Claim 13, delete "he" and insert --be-- therefor

Signed and Sealed this
Twenty-fifth Day of October, 2022

*Katherine Kelly Vidal*

Katherine Kelly Vidal
*Director of the United States Patent and Trademark Office*